US007338794B2

(12) United States Patent
Gaertner et al.

(10) Patent No.: US 7,338,794 B2
(45) Date of Patent: Mar. 4, 2008

(54) AMENDED RECOMBINANT CELLS FOR THE PRODUCTION AND DELIVERY OF GAMMA INTERFERON AS AN ANTIVIRAL AGENT, ADJUVANT AND VACCINE ACCELERANT

(75) Inventors: Frank H. Gaertner, San Diego, CA (US); Stacey Lynn Lee, San Diego, CA (US); Robert W. Shutter, Poway, CA (US)

(73) Assignee: Dow Agrosciences LLC, Indianapolis, IN (US)

( * ) Notice: Subject to any disclaimer, the term of this patent is extended or adjusted under 35 U.S.C. 154(b) by 534 days.

(21) Appl. No.: 10/681,540

(22) Filed: Oct. 7, 2003

(65) Prior Publication Data
US 2004/0146484 A1 Jul. 29, 2004

Related U.S. Application Data

(60) Provisional application No. 60/417,124, filed on Oct. 8, 2002.

(51) Int. Cl.
*C12N 1/20* (2006.01)
*A61K 39/108* (2006.01)
*C07K 14/00* (2006.01)

(52) U.S. Cl. ............................. 435/252.34; 424/260.1; 530/351; 530/350

(58) Field of Classification Search ..................... None
See application file for complete search history.

(56) References Cited

U.S. PATENT DOCUMENTS

| 4,432,895 A * | 2/1984 | Tarnowski ................. 530/351 |
| 4,695,455 A | 9/1987 | Barnes et al. |
| 4,695,462 A | 9/1987 | Barnes et al. |
| 5,281,532 A | 1/1994 | Rammler et al. |
| 6,121,247 A | 9/2000 | Huang et al. |

OTHER PUBLICATIONS

Steidler, L. (2002) "In situ delivery of cytokines by genetically engineered *Lactococcus lactis*" Antonie van Leeuwenhoek 82:323-331.
Steidler, L. et al. (1998) "Mucosal delivery of murine interleukin-2 (IL-2) and IL-6 by recombinant strains fo *Lactococcus lactis* coexpressing antigen and cytokine" *Infection and Immunity* 66(7):3183-3189.
Carrier, M.J. et al. (1992) "Expression of human IL-1β in *Salmonella typhimurium*. A model system for the delivery of recombinant therapeutic proteins in vivo" *J. Immunol.* 148(4):1176-1181.
Ada, G. et al. Overview of Host Defense Mechanisms with Special Reference to Viral Infections, *Gamma Interferon in Antiviral Defense*, 1997, pp. 1-18, Chapman & Hall, New. York.
Anderson, K.P. et al. "Enhancement Of a Secondary Antibody Response to Vesicular Stomatitis Virus 'G' Protein By IFN-Gamma Treatment at Primary Immunization", *J.Immunol.*, 1988, pp. 3599-3604, vol. 140, No. 10.
Babiuk, L.A. et al. "Application of Interferons In The Control of Infectious Diseases of Cattle", *Journal of Dairy Science*, 1991, pp. 4385-4398, vol. 74, No. 12.

Cerretti, D.P., et al. "Cloning, Sequence, and Expression of Bovine Interferon-Gamma", *J.Immunol.*, 1986, pp. 4561-4564, vol. 136, No. 12.
Fox, L.K., et al. "The Effect Of Interferon-Gamma Intramammary Administration on Mammary Phagocyte Function", *J. Vet. Med B*, 1990, pp. 28-30, vol. 37, Paul Parey Scientific Publishers, Berlin and Hamburg.
Fransen, L. et al. "Recombinant Tumor Necrosis Factor: Species Specificity For a Variety of Human and Murine Transformed Cell Lines", *Cell. Immunol.*, 1986, pp. 260-267, vol. 100.
Friedman, R.M. et al. "Interferons with Special Emphasis on the Immune System", *Adv. Immunol.*, 1983, pp. 97-140, Vol. 34.
Gaertner, F.H. et al. "CellCap: An Encapsulation System for Insecticidal Biotoxin Proteins", *Advanced Engineered Pesticides*, 1993, pp. 73-83, Marcel Dekker, New York.
Gough, R.E., et al., "Further Studies On The Adjuvant Effect Of an Interferon Inducer (Brl-5907) on Newcastle Disease and Avian Influenza Inactivated Vaccines", *Res. Vet. Sci.*, 1975, pp. 185-188, vol. 19.
Gresser, I., et al. "Anti-Tumor Effects of Interferon In Mice Injected With Interferon-Sensitive and Interferon-Resistant Friend Leukemia Cells. VI. Adjuvant Therapy After Surgery in the Inhibition of Liver and Spleen Metastases", *Int. J. Cancer*, 1987, pp. 789-792, vol. 39.
Knight Jr., E., "Antiviral and Cell Growth Inhibitory Activities Reside In The Same Glycoprotein Of Human Fibroblast Interferon", *Nature*, 1976, pp. 302-303, vol. 262.
Lofthouse, S.A. et al. "Cytokines as Adjuvants For Ruminant Vaccines", *International Journal for Parasitology*, 1996, pp. 835-842, vol. 26, No. 8/9.
Michalski, W.P. et al. "Recombinant Chicken IFN-Gamma Expressed In *Escherichia coli*: Analysis Of C-Terminal Truncation and Effect on Biologic Activity", *J. Interferon Cytokine Res.*, 1999, p. 383-392, vol. 19.
Opdenakker, G. et al. "Interaction of Interferon With Other Cytokines", *Experientia*, 1989, pp. 513-520, vol. 45.
Perussia, B., et al. "Immune Interferon Induces The Receptor For Monomeric IgG1 on Human Monocytic and Myeloid Cells", *J. Exp. Med.*, 1983, pp. 1092-1113, vol. 158.
Pestka, S., et al. "Interferons and Their Actions", *Annu. Rev. Biochem.*, 1987, pp. 727-777, vol. 56.
Pighetti, G.M., et al. "Specific Immune Responses of Dairy Cattle After Primary Inoculation with Recombinant Bovine Interferon-Gamma as an Adjuvant When Vaccinating Against Mastitis", *American Journal of Veterinary Research*, 1996, p. 819-824, vol. 57, No. 6.

(Continued)

*Primary Examiner*—Nancy Vogel
(74) *Attorney, Agent, or Firm*—Saliwanchik, Lloyd & Saliwanchik

(57) ABSTRACT

The present invention provides active cytokine and/or chemokine compositions, as well as inexpensive means for the production, amended-cell encasement of active cytokine and/or chemokine compositions, processing, and delivery of active cytokine and/or chemokine compositions. The subject invention also provides methods of treatment and methods of accelerating an immune response comprising the administration of amended recombinant cell (ARC) containing cytokine and/or chemokine compositions to animals or humans.

20 Claims, 10 Drawing Sheets

OTHER PUBLICATIONS

Sordillo, L.M., et al. "Controlling Acute *Escherichia coli* Mastitis During the Periparturient Period with Recombinant Bovine Interferon-Gamma", *Veterinary Microbiology*, 1991, pp. 189-198, vol. 28.

Steinbeck, M.J., et al. "Activation of Bovine Neutrophils By Recombinant Interferon-Gamma", *Cell. Immunol.*, 1986, pp. 137-144, vol. 98.

Vilcek, J., et al. "Interferon and the Immune System", *Interferon*, 1984, vol. 2, Elsevier, Amsterdam.

Yilma, T.K. et al. "Expression of an Adjuvant Gene (Interferon-Gamma) in Infectious Vaccinia Virus Recombinants", *Vaccines 87: Modern Approaches to New Vaccines*, 1987, pp. 393-396, Cold Spring Harbor, New York.

Yilma, T. et al. "Enhancement of Primary and Secondary Immune Responses By Interferon-Gamma", *Adv.Exp.Med.Biol.* 1989, pp. 145-152, vol. 251.

Yip, Y.K., et al. "Purification and Structural-Functional Characterization of Human Immune Interferon", *J. Biol. Chem.*, 1984, p. 283, vol. 3.

Zuffa, A. et al. "Protection of Cattle Vaccinated With Inactivated Oil Adjuvant Infectious Bovine Rhino Tracheitis Vaccine Against Experimental Infection", *Zbl. Vet. Med. B.*, 1980, pp. 725-733, vol. 27.

\* cited by examiner

```
      agagaactagtaaaaaggagaaatccATGCAGGGCCAATTTTTTAGA
1     ---------+---------+---------+---------+-------  47
      tctcttgatcatttttcctctttaggTACGTCCCGGTTAAAAAATCT

M  Q  G  Q  F  F  R

GAAATAGAAAACTTAAAGGAGTATTTTAATGCAAGTAGCCCAGATGTAGCTAAGGGTGGG
48    ---------+---------+---------+---------+ ---------+---------+ 107
      CTTTATCTTTTGAATTTCCTCATAAAATTACGTTCATCGGGTCTACATCGATTCCCACCC

E  I  E  N  L  K  E  Y  F  N  A  S  S  P  D  V  A  K  G  G

CCTCTCTTCTCAGAAATTTTGAAGAATTGGAAAGATGAAAGTGACAAAAAAATTATTCAG
108   ---------+---------+---------+---------+---------+---------+ 167
      GGAGAGAAGAGTCTTTAAAACTTCTTAACCTTTCTACTTTCACTGTTTTTTTAATAAGTC

P  L  F  S  E  I  L  K  N  W  K  D  E  S  D  K  K  I  I  Q

AGCCAAATTGTCTCCTTCTACTTCAAACTCTTTGAAAACCTCAAAGATAACCAGGTCATT
168   ---------+---------+---------+---------+---------+---------+ 227
      TCGGTTTAACAGAGGAAGATGAAGTTTGAGAAACTTTTGGAGTTTCTATTGGTCCAGTAA

S  Q  I  V  S  F  Y  F  K  L  F  E  N  L  K  D  N  Q  V  I

CAAAGGAGCATGGATATCATCAAGCAAGACATGTTTCAGAAGTTCTTGAATGGCAGCTCT
228   ---------+---------+---------+---------+---------+---------+ 287
      GTTTCCTCGTACCTATAGTAGTTCGTTCTGTACAAAGTCTTCAAGAACTTACCGTCGAGA

Q  R  S  M  D  I  I  K  Q  D  M  F  Q  K  F  L  N  G  S  S

GAGAAACTGGAGGACTTCAAAAAGCTGATTCAAATTCCGGTGGATGATCTGCAGATCCAG
288   ---------+---------+---------+---------+---------+---------+ 347
      CTCTTTGACCTCCTGAAGTTTTTCGACTAAGTTTAAGGCCACCTACTAGACGTCTAGGTC

E  K  L  E  D  F  K  K  L  I  Q  I  P  V  D  D  L  Q  I  Q

CGCAAAGCCATAAATGAACTCATCAAAGTGATGAATGACCTGTCACCAAAATCTAACCTC
348   ---------+---------+---------+---------+---------+---------+ 407
      GCGTTTCGGTATTTACTTGAGTAGTTTCACTACTTACTGGACAGTGGTTTTAGATTGGAG

R  K  A  I  N  E  L  I  K  V  M  N  D  L  S  P  K  S  N  L

AGAAAGCGGAAGAGAAGTCAGAATCTCTTTCGAGGCCGGAGAGCATCAACGtaatgactcgagtctct
408   ---------+---------+---------+---------+---------+---------+-------- 475
      TCTTTCGCCTTCTCTTCAGTCTTAGAGAAAGCTCCGGCCTCTCGTAGTTGCattactgagctcagaga

BGI/ARC Stability Assay
Key to –80oC samples and their corresponding protein and activity values

| Temperature Treatment | Sample Name | Timepoints | Gel Scan Values | Sample Activity Titer (averaged) |
|---|---|---|---|---|
| -20°C | A1 | 2 days | 2051.3 | 100,000 |
| -20°C | A2 | 4 days | 2051.4 | 100,000 |
| -20°C | A3 | 8 days | 1586.8 | 200,000 |
| -20°C | A4 | 17 days | 1851.9 | 300,000 |
| -20°C | A5 | 3 months | 1959.7 | 300,000 |
| -20°C | A6 | 6 months | 2059.5 | 300,000 |
| 4°C | B1 | 2 days | 1967.1 | 300,000 |
| 4°C | B2 | 4 days | 2194.1 | 300,000 |
| 4°C | B3 | 8 days | 2119 | 300,000 |
| 4°C | B4 | 17 days | 1914.6 | 200,000 |
| 4°C | B5 | 3 months | 2083.8 | 300,000 |
| 4°C | B6 | 6 months | 2415.8 | 300,000 |
| RT | C1 | 2 days | 3336.7 | 165,000 |
| RT | C2 | 4 days | 2686.9 | 300,000 |
| RT | C3 | 8 days | 2469.9 | 300,000 |
| RT | C4 | 17 days | 2723 | 200,000 |
| RT | C5 | 3 months | 2966.3 | 20,000 |
| RT | C6 | 6 months | 2803.1 | 30,000 |
| 37°C | D1 | 2 days | 2127.6 | 65,000 |
| 37°C | D2 | 4 days | 2711.1 | 200,000 |
| 37°C | D3 | 8 days | 2674.6 | 65,000 |
| 37°C | D4 | 17 days | 2958.9 | 65,000 |
| 37°C | D5 | 3 months | 1524.8 | 20,000 |
| 37°C | D6 | 6 months | 1099.7 | 65,000 |
| N/A | E1 | T=0 | 3021.3 | 30,000 |
| N/A | E2 | CGI | N/A | 6500 |
| -20°C storage | Positive Control | N/A | Equivalent to E1 | 200,000 |
| -20°C storage | Negative Control | N/A | 0 | 1,000 |

FIG. 5

# AMENDED RECOMBINANT CELLS FOR THE PRODUCTION AND DELIVERY OF GAMMA INTERFERON AS AN ANTIVIRAL AGENT, ADJUVANT AND VACCINE ACCELERANT

CROSS REFERENCE TO RELATED APPLICATION

This application claims the benefit of U.S. Provisional Application 60/417,124, filed Oct. 8, 2002, which is hereby incorporated by reference in its entirety, including all figures, tables, sequences, and formulae.

BACKGROUND OF THE INVENTION

Cytokines and chemokines are important elements of functional immune systems. For example, interferon is one of biotechnology's first recombinant drugs and is used as an antiviral agent and immunoadjuvant for vaccines in animal health (2;24). Gamma interferon (IFN-γ) is a cytokine that elicits potent antiviral and immunoadjuvant responses in animals (1-3;6;8;13;17;18;20;22;23;25). IFN-γ-enhanced vaccines (13;18) are useful in the treatment of diseases such as, for example, shipping fever and mastitis in cattle. However, under current technology IFN-γ has proven to be both unstable and extremely expensive to produce. With costs in the hundreds of dollars per milligram, and required treatment levels in multiple milligrams per dose, the use of IFN-γ as an animal health antiviral agent or as a vaccine adjuvant is deemed impractical. The initial promise of the interferons and other cytokines (set forth in Table I), as magic bullets for curing disease, has yet to be fully realized (1).

In cattle and other animals, such as other mammals, birds, fish, and reptiles, IFN-γ acts either directly or indirectly on almost every component of the innate and adaptive immune systems (1). In addition, IFN-γ is one of the most, if not the most, pleotropic of the cytokines, profoundly affecting antigen processing and presentation, inhibition of lymphocyte migration, macrophage activation, B-lymphocyte antibody production (21), natural killer (NK) cell activity, and upregulation of leukocyte cell-surface molecules for trafficking and immune recognition. Strong receptors for IFN-γ are located on T and B-lymphocytes, NK-cells, monocytes, macrophage, fibroblasts, neutrophils, endothelial cells, and smooth muscle cells. Also, because of its central role as an antiviral agent, IFN-γ is a major target for viral subversive activity. For example, viruses encode proteins that can inactivate IFN-γ, interfere with IFN-induced antiviral pathways, and interrupt intracellular IFN-γ signaling.

Biologically active bovine IFN-γ was first cloned and synthesized in *Escherichia coli* in 1986 (5). The nucleotide sequence of equine IFN-γ was reported in 1994, showing a sequence identity of 67% to human and 78% to bovine IFN-γ. The structure of recombinant chicken IFN-γ was reported in 1999, and an active, truncated form (truncated at lys 133) was expressed in *E. coli*. The 3-D structure was shown to be similar to bovine and human IFN-γ, despite an overall amino acid identity of only 32% (14).

BRIEF SUMMARY OF THE INVENTION

The present invention provides active cytokine and/or chemokine compositions, as well as inexpensive means for the production, amended-cell encasement of active cytokine and/or chemokine compositions, processing, and delivery of active cytokine and/or chemokine compositions. The subject invention also provides methods of treatment and methods of accelerating an immune response comprising the administration of active gamma-interferon, and other cytokine and/or chemokine compositions to animals or humans.

In one aspect of the invention, IFN-γ, as well as other cytokines, can be expressed in a wide variety of microbial cells, including the bacterium *Pseudomonas fluorescens*, through the use of genetic engineering techniques well known in the art. Appropriately reconstructing the cytokine gene and positioning it precisely in a host plasmid-vector between a strong regulated promoter and transcription/translation terminators, routinely accomplishes the expression of IFN-γ in a particular foreign host. The suitability of any such host is also routine to test by ordinary means by one of ordinary skill in the art, without undue experimentation. Once the transformed microbial cells have expressed the IFN-γ or other cytokines to a high level, the cells can be amended with agents, including heat and chemical agents, that kill (sterilize) the cells, stabilize an expressed active cytokine, and amend the cell wall for optimal release of the cell-encased cytokine. For example, the sterilization/amendment procedure used in the present description for the cells of *Pseudomonas fluorescens*, expressing IFN-γ, is a modification of a process originally used for the production of a commercial biopesticide, MVP (4;9;19). According to this method, the cells of *P. fluorescens* are treated with Lugol iodine at a pH of about 4.3. This pH thoroughly sterilizes the culture in situ, amends the cell wall for physical durability, and renders the bacterial cell wall susceptible to proteolytic dissolution (9). The procedure also eliminates cellular flocculation, and appears to decrease the endotoxic properties of the *Pseudomonas* cell wall.

IFN-γ containing amended recombinant cells (IFN-γ/ARCs) can be delivered by oral, nasal, ocular or parental injection means. Such methods of inoculation of IFN-γ/ARCs can be used to treat diseases in humans and animals; for example in cattle, ARCs containing bovine IFN-γ can be used as prophylactics to guard against shipping fever, or used with dams of cattle to protect newborns from viral disease and/or bacterial gastroenteritis. In addition, humans and animals other than cattle can be so treated, such as horses, pigs, chickens, as well as household pets. The method is also applicable for curtailing various stress-related diseases in animals and humans as well as for enhancing, as an adjuvant and accelerant of the immune response, multi-route human vaccinations via the administration of IFN-γ containing ARCs in amounts sufficient to induce a desired biological effect.

BRIEF DESCRIPTION OF THE DRAWINGS

FIG. 1 is a plasmid map of pMYC1803.

FIG. 2 is the coding sequence, complementary sequence, and amino acid sequence for synthetic bovine gamma-interferon, minus signal peptide (SEQ ID NO:1, 2 and 3, respectively).

FIG. 3 is a photograph of a SDS-PAGE showing major bands of α and γ bovine interferon at about 18 and 17 kDa respectively. Culture samples were diluted 1:5 prior to loading the gel. 10 μL was added per well.

FIG. 4 is a photograph of a sodium dodecyl sulfate polyacrylamide gel electrophoresis (SDS-PAGE) experiment of a French-Press disrupted *P. fluorescens* culture containing both BAI and BGI, showing that the bulk of the BAI appears in the pellet fraction.

FIG. 5 is a tabular illustration of BGI/ARC stability assay results.

FIG. 6A is a graphical representation of the MHC II protein produced from bovine kidney cells in vitro in response to homogeneous bovine IFN-γ (BGI) purified from recombinant *Eschericia coli*. FIG. 6B is a graphical comparison of the MHC II protein produced from bovine kidney cells in vitro in response to 1.) untransformed *P. fluorescens*, MB324 (ARC minus vector, minus BGI), 2.) transformed *P. fluorescens*, MR1241 (ARC plus vector, minus BGI), 3.) transformed *P. fluorescens*, MR1605 (BGI/ARC, ARC plus vector, plus BGI), and 5.) BGI purified from recombinant *P. fluorescens*.

FIG. 7A illustrates the effects of purified recombinant BGI (RecBoIFNγ) from *E. coli* on the production of MHC II protein from dendritic cells. FIG. 7B is a comparison of MHCII production by dendritic cells in response to 1.) untransformed *P. fluorescens*, host-cell control (MB324), 2.) pMYC1803 (transformed with vector only) ARC control (MR1241), 3.) BGI/ARC (transformed with BGI gene) (MR1605), and 4.) purified BGI from *P. fluorescens* (DOW-IFN)

Figure 12:
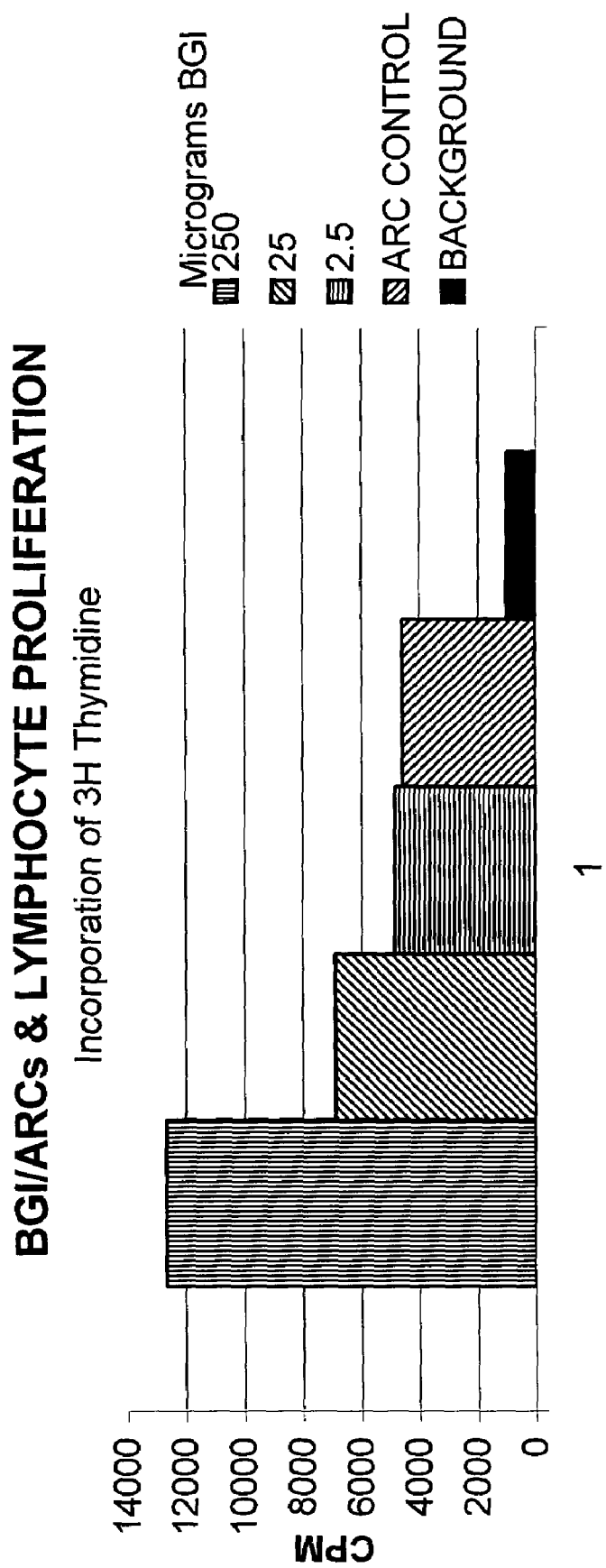

FIG. 12 demonstrates the proliferative effects of BGI/ARCs on lymphocytes (as measured by the incorporation of $^3$H thymidine).

Figure 13:
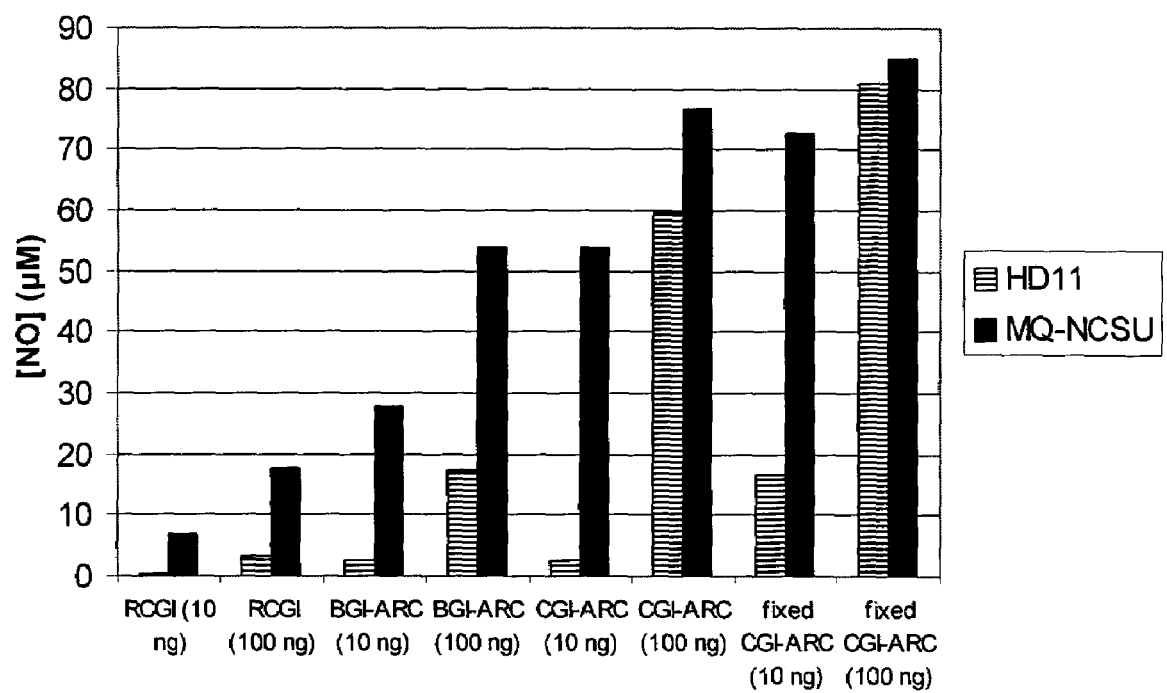

FIG. 13 illustrates the activity of avian IFN-γ/ARCs (CGI/ARCs) on chicken macrophage nitric oxide (NO) production.

DETAILED DESCRIPTION OF THE INVENTION

The subject invention provides active cytokine and/or chemokine compositions that have been expressed in processed (amended) microbial systems, named herein, Amended Recombinant Cells or ARCs. ARCs are recombinant microbial cells containing expressed, heterologous proteins, the cells of which have been killed through specific chemical-sterilization processes that amend the cell wall of the microbial cells. The amendment process simultaneously alters the properties of the cell walls of the microbes in two distinct ways: A.) Physical strengthening of the cell wall occurs, making the microbial cells harder to rupture by i.) sheering, ii.) sonic oscillation, or iii.) pressure-cell disruption, and B.) Chemical denaturing of the protein of the cell wall occurs, making the cells easier to rupture by proteolytic hydrolysis.

In various embodiments, the subject invention provides microbial ARCs that are transformed with vectors comprising at least one heterologous gene encoding IL-1, IL-2, IL-3, IL-4, IL-5, IL-6, IL-7, IL-8, IL-9, IL-10, IL-11, IL-15, Il-16, Il-18, IL-23, IL-24, erythropoietin, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-γ, IFN-α, IFN-β); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1), or chemokines (such as, but not limited to, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROP, MIP-3α/Exodus/LARC, MIP-3β/Exodus-3/ELC, MIP-4/PARC/DC-CK1, PF-4, RANTES, SDF1α, TARC, or TECK) or those cytokines and/or chemokines provided in Tables 1, 8 and 9. In a preferred embodiment, ARCs contain IFN-γ (e.g., bovine, avian (e.g., chicken), fish, or human IFN-γ). In another preferred embodiment, ARCs comprise IFN-γ and IFN-α (e.g., bovine, avian (e.g., chicken), fish, or human fish IFN-γ and IFN-α). As used herein, the terms "ARC" or "ARCs" indicate amended recombinant cells that contain one or more heterologous genes. Amended recombinant cells containing no heterologous interferon genes or interferon protein are referred to as "Control ARCs" or "ARC controls".

In some embodiments microbial cells co-express one or more other heterologous genes, encoding antigens and/or antigenic proteins. Non-limiting examples of antigens or antigenic proteins include, and are not limited to, autoantigens, tumor antigens, MMR vaccines, polio vaccines, tetanus vaccines, pathogens normally encountered by an individual in the environment (e.g., food borne pathogens such as *Klebsiella, Salmonella, Escherichia* spp., hepatitis viruses, influenza viruses, etc.) and pathogenic substances specifically introduced into the environment of the individual, such as a biotoxin (e.g., mycotoxins, such as trichothecene mycotoxin (T-2), Staphylococcal enterotoxin B, ricin, or *Clostridium botulinum* neurotoxin, weaponized microbial cells (e.g., viruses containing toxin DNA or RNA inserts, or bacterial or fungal cells transformed with toxins [e.g., mycotoxins, such as trichothecene mycotoxin (T-2), Staphylococcal enterotoxin B, ricin, or *Clostridium botulinum* neurotoxin], viral pathogens, fungal pathogens, or bacterial pathogens (e.g., smallpox, anthrax, Ebola virus, *Yersinia pestis*), or immunomodulatory proteins, such as superantigens, serum albumins, or protein stabilizers. Various embodiments provide for individual ARC compositions expressing a single heterologous gene (e.g., a single cytokine, chemokine, or protein). In certain embodiments, the co-expressed protein or antigen, such as serum albumin, is encoded by DNA derived from a desired species of animal. Some embodiments provide that all proteins expressed in a microbial system are contained in a single vector. Other embodiments provide for the transformation of microbial cells with multiple vectors encoding the desired proteins. In yet other embodiments, the heterologous gene(s) may be introduced into the host in any convenient manner, either providing for extrachromosomal maintenance or integration into the host genome. (By heterologous is intended that the gene is not present in the host into which it is introduced, nor would the gene normally be found in such host. That is, even if the host organism and the source of the heterologous gene exchange information, the heterologous gene would normally not be found in the wild-type host cells in nature. Usually, the term heterologous will involve species of different genera as host and gene source.)

Various constructs may be used, which include replication systems from plasmids, viruses, or centromeres in combination with an autonomous replicating segment (ars) for stable maintenance. Where only integration is desired, constructs can be used which may provide for replication, and are either transposons or have transposon-like insertion activity or provide for homology with the genome of the host. Frequently, DNA sequences are employed having the heterologous gene between sequences which are homologous with sequences in the genome of the host, either chromosomal or plasmid. Desirably, the heterologous gene(s) will be present in multiple copies. See for example, U.S. Pat. No. 4,399,216. Thus, conjugation, transduction, transfection and transformation may be employed for introduction of the heterologous gene.

In embodiments where an extrachromosomal element is employed, the DNA construct will desirably include a marker that allows for a selection of those host cells containing the construct. The marker is commonly one which provides for biocide resistance, e.g., antibiotic resistance or heavy metal resistance, complementation providing prototrophy to an auxotrophic host, or the like. The replication systems can provide special properties, such as runaway replication, can involve cos cells, or other special feature.

Heterologous gene(s), having transcriptional and translational initiation and termination regulatory signals recognized by the host cell, can be employed in conjunction with the heterologous gene. However, in those situations where the heterologous gene is modified, as for example, removing a leader sequence or providing a sequence which codes for the mature form of the cytokine and/or chemokine, where the entire gene encodes for a precursor, it will frequently be necessary to manipulate the DNA sequence, so that a transcriptional initiation regulatory sequence may be provided which is different from the natural one.

A wide variety of transcriptional initiation sequences exist for a wide variety of hosts. The sequence can provide for constitutive expression of the cytokine and/or chemokine or regulated expression, where the regulation may be inducible by a chemical, e.g., a metabolite, by temperature, or by a regulatable repressor. See for example, U.S. Pat. No. 4,374,927 which is hereby incorporated by reference in its entirety. The particular choice of the promoter will depend on a number of factors, the strength of the promoter, the interference of the promoter with the viability of the cells, the effect of regulatory mechanisms endogenous to the cell on the promoter, and the like. A large number of promoters are available from a variety of sources, including commercial sources.

Vectors suitable for expression of the cytokines set forth in Tables 1, 8, and 9 are well known to those skilled in the art. Likewise, heterologous genes encoding the cytokines and chemokines set forth in Tables 1, 8, and 9 are known to those skilled in the art and coding sequences may be obtained from a variety of sources, including various patent databases, publicly available databases (such as the nucleic acid and protein databases found at the National Library of Medicine or the European Molecular Biology Laboratory) that contain nucleic acid or polypeptide sequences encoding the aforementioned cytokines, chemokines, or other proteins, the scientific literature, or scientific literature cited in catalogs produced by companies such as Genzyme, Inc., R&D Systems, Inc, or InvivoGen, Inc. [see, for example, the 1995 Cytokine Research Products catalog, Genzyme Diagnostics, Genzyme Corporation, Cambridge Mass.; 2002 or 1995 Catalog of R&D Systems, Inc (Minneapolis, Minn.); or 2002 Catalog of InvivoGen, Inc (San Diego, Calif.) each of which is incorporated by reference in its entirety, including all references cited therein]. Alternatively, nucleic acids encoding cytokines and/or chemokines and vectors containing nucleic acids encoding cytokines and/or chemokines can be obtained from commercial vendors, such as R&D Systems, Inc. (Minneapolis, Minn. 55413) or InvivoGen, Inc. (San Diego, Calif. 92121). In some aspects of the subject invention, microbial cells are manipulated to express various combinations of cytokines and/or chemokines.

Microbial cells suitable for use in the subject invention include prokaryotes (both Gram positive and Gram negative organisms) and lower eukaryotes, such as fungi. Species of bacterial cells suitable for use in the instant invention include those of the genera: 1) *Enterobacteriaceae*, including the species of the genera *Escherichia, Erwinia, Shigella, Salmonella*, and *Proteus*; 2) *Bacillaceae*; 3) *Rhizobiaceae*, such as *Rhizobium*; 4) *Spirillaceae*, such as photobacterium, *Zymomonas, Serratia, Aeromonas, Vibrio, Desulfovibrio, Spirillum*; 6) *Lactobacillaceae*; 7) *Pseudomonadaceae*, such as *Pseudomonas* and *Acetobacter*; 8) *Azotobacteraceae* and *Nitrobacteraceae*. Among lower eukaryotes, fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like. Once the transformed microbial cells have expressed the cytokine proteins to a high level, the cells can be harvested by conventional means and treated with fixation reagents to kill the cells and stabilize the active cytokine. In certain embodiments, cytokines and/or chemokines are expressed in *Pseudomonas fluorescens* cells; the cells are fixed, harvested and washed or optionally, washed, and then fixed.

The cellular host containing one or more heterologous genes may be grown in any convenient nutrient medium, where the DNA construct provides a selective advantage (e.g., growth in a selective medium containing antibiotics), providing for a selective medium so that substantially all or all of the cells retain the heterologous gene(s). These cells may then be harvested in accordance with conventional ways and modified in the various manners described above. Alternatively, the cells can be fixed prior to harvesting.

ARCs are defined here and throughout this invention by the following tests: A.) ARCs are dead. They are unable to form colonies on nutrient media suitable for the growth of their live forms. B.) ARCs have enhanced physical durability. They resist disruption by sonic oscillation, or rupture by passage through a French Pressure Cell better than their unamended, living forms. C.) ARCs are susceptible to dissolution by proteolysis. They can be shown, microscopically, optically, or by other means to be more susceptible to proteolytic dissolution by trypsin (or a wide variety of other proteases) than their unamended, living forms. D.) ARCs contain recombinant, heterologous genes and express heterologous proteins, wherein the desired functional properties of the heterologous proteins are either partially or fully maintained.

Various techniques for inactivating and amending the host cells include acidification with acids, such as acetic acid, with or without the addition of a halogenating agent, such as iodine, UV irradiation; lyophilization; toxins, e.g., antibiotics; phenols; anilides, e.g., carbanilide and salicylanilide; hydroxyurea; quaternary alcohols; antibacterial dyes; EDTA and amidines; non-specific organic and inorganic chemicals, such as the already mentioned halogenating agents, e.g., chlorinating, brominating or iodinating agents; aldehydes, e.g., glutaraldehyde or formaldehyde; toxic gases, such as ozone and ethylene oxide peroxide; psoralens; desiccating agents; or the like, which may be used individually or in combination. The choice of agent will depend upon the particular cytokine or chemokine, the nature of the host cell, and the nature of the modification of the cellular structure required to produce the desired effects of killing the cell, preserving the cytokine activity, physically strengthening the cell wall, and chemically denaturing the proteins of the cell wall, rendering the cells more sensitive to proteolysis.

Suitable agents for inactivation and amendment to produce ARCs include halogenating agents, particularly halogens of atomic numbers 17-80. More particularly, iodine can be used under mild conditions and for sufficient time to achieve the desired results. Other suitable techniques include treatment with aldehydes, such as formaldehyde and glutaraldehyde anti-infectives, such as zephiran chloride and cetylpyridinium chloride alcohols, such as isopropyl and ethanol various histologic fixatives, such as Bouin's fixative and Helly's fixative (See: Humason, Gretchen L., Animal Tissue Techniques, W. H. Freeman and Company, 1967); or a combination of physical (heat) and chemical agents that prolong the activity of the cytokine and/or chemokine.

For halogenation with iodine, temperatures will generally range from about 0° C. to 50° C., but the reaction can be carried out at room temperature. It is a routine matter for one of ordinary skill in the art to determine the optimum range for these variables based on the activity or lack there of with respect to the cytokine expressed by the respective ARCs. Other such variables may be tested, as well, by one of ordinary skill without undue experimentation. For example, conveniently, iodination may be tested using triiodide or iodine at 0.5 to 5% in an acidic aqueous medium, particularly an aqueous carboxylic acid solution that may vary from about 0.5-5M. Acetic acid may be used, or other carboxylic acids, generally of from about 1 to 4 carbon atoms, may also be employed. The time for the reaction will generally range from less than a minute to about 24 hrs, usually from about 1 to 6 hours; typically, the pH of the halogenation (e.g., iodination) solutions is maintained between at about 4.0 and about 7.0. In certain embodiments, the pH ranges from about 4.0 to about 6.0, about 4.0 to about 5.0, about 4.1 to 4.7, about 4.2 to 4.6, about 4.3 to 4.4, or about 4.3. In other embodiments, the pH ranges from about 3.0 to about 6.0, about 3.5 to about 5.0, about 3.7 to 4.7, about 3.8 to 4.6, about 3.9 to 4.4, or about 4.3. Any residual iodine may be removed, if necessary, by reaction with a reducing agent, such as dithionite, sodium thiosulfate, or other reducing agent. In addition, the modified cells may be subjected to further treatment, such as exhaustive washing to remove all of the reaction medium, isolation in dry form, and formulation with typical stickers, spreaders, and adjuvants generally utilized by those skilled in the art. In certain embodiments, ARCs can be prepared by treating them with crosslinking agents known in the art.

Procedures for one such amendment process, Lugol fixation, has been described in (9) and U.S. Pat. No. 4,695,455 (which are hereby incorporated by reference in their entirety). Once amended, the cells are washed in water and appropriately formulated for use in a variety of therapeutic applications. In this aspect of the invention, compositions containing amended organisms are prepared and can be administered to an individual in amounts sufficient to induce a desired biological effect. Compositions may be formulated in any carriers, including for example, carriers described in E. W. Martin's *Remington's Pharmaceutical Science*, Mack Publishing Company, Easton, Pa.

The subject invention provides methods of inducing and/or accelerating an immune response in an individual comprising the steps of administering to an individual (such as an avian, amphibian, reptilian, shellfish, fish, or mammalian individual) a composition comprising cytokine/chemokine-expressing amended recombinant cells (ARCs), an antigen or antigens of interest, and, optionally, additional adjuvanting molecules such as lipopolysaccharide (LPS) or CpG dinucleotide in an amount effective to engender an immune response. In certain preferred embodiments, the ARCs co-express: a) one or more antigen of interest, and b) one or more cytokine/chemokine, such as INF-γ or other cytokines/chemokines set forth in Tables 1, 8, and 9. In other embodiments, a composition comprising an admixture of one or more antigen and ARCs expressing one or more cytokine/chemokine are provided to an individual. For the purposes of the admixture composition, antigen(s) is/are provided: 1) in a purified form, 2) as a crude extract, and/or 3) in a separate ARC composition wherein the cells have been transformed with DNA encoding an antigen of interest. In any embodiment, adjuvants known to those skilled in the art can be, optionally, provided. In certain preferred embodiments, ARCs co-express, at least, both IFN-γ and IFN-α.

Another aspect of the subject invention provides methods of accelerating the immune response of an individual comprising the administration of amended recombinant cells (ARCs) comprising one or more cytokine and/or chemokine, or compositions thereof, to an individual in amounts effective to accelerate the immune response of the individual. In one aspect of this invention, the development of a peak humoral immune response (e.g., maximal amounts of IgM and/or IgG antibodies observed after antigenic challenge) of an individual can be accelerated by one to 14 days or more. In this aspect of the invention, the individual can have had prior exposure to an antigen or the antigen can be co-administered to the individual.

Thus, the subject invention provides methods of accelerating the development of antibody isotypes (e.g., IgG1 and IgG2), or various classes of antibodies (e.g., IgM, IgG, IgA, IgE, and/or IgY) in an individual comprising the administration of compositions comprising ARCs containing one or more cytokine and/or chemokine. The method may further comprise the administration of an antigen or immunogen prior to, concurrent with, or subsequent to the administration of an ARC composition. In some embodiments, the ARC composition is an IFN-γ/ARC. Other embodiments provide ARCs that contain both IFN-α and IFN-γ. In various embodiments the interferon genes are of human, avian (e.g., chicken), bovine, mammalian, or fish origin.

In certain embodiments of this invention, ARCs expressing one or more cytokine and/or chemokine are administered to an individual within two to one hundred and sixty-eight hours after exposure to an antigen of interest. "An antigen of interest" includes, and is not limited to, autoantigens, tumor antigens, MMR vaccines, polio vaccines, tetanus vaccines, pathogens normally encountered by an individual in the environment (e.g., food borne pathogens such as *Klebsiella, Salmonella, Escherichia* spp., hepatitis viruses, influenza viruses, etc.) and pathogenic substances specifically introduced into the environment of the individual, such as a biotoxin (e.g., mycotoxins, such as trichothecene mycotoxin (T-2), Staphylococcal enterotoxin B, ricin, or *Clostridium botulinum* neurotoxin, weaponized microbial cells (e.g., viruses containing toxin DNA or RNA inserts, or bacterial or fungal cells transformed with toxins [e.g., mycotoxins, such as trichothecene mycotoxin (T-2), Staphylococcal enterotoxin B, ricin, or *Clostridium botulinum* neurotoxin], viral pathogens, fungal pathogens, or bacterial pathogens (e.g., smallpox, anthrax, Ebola virus, *Yersinia pestis*), or immunomodulatory proteins, such as superantigens, serum albumins, or protein stabilizers. Thus, the subject invention is applicable to both: a) the treatment of an individual exposed to a biologic agent used in the commission of an act of bioterrorism; and b) the treatment of an individual exposed to a pathogen normally encountered in the environment. In preferred embodiments of this aspect of the invention, ARCs co-express IFN-γ, and/or IFN-α, and optionally, LPS. Optionally, ARCs co-express other proteins, cytokines, and/or chemokines in addition to IFN-γ and IFN-α.

The subject invention also provides methods of treating tumors, cancers, or malignancies comprising the administration of amended recombinant cells (ARCs) comprising one or more cytokine and/or chemokine, or compositions thereof, to an individual in amounts effective to effect a therapeutic effect in an individual. In some embodiments, the term "treatment" and/or "therapeutic effect" refers to any process, action, application, therapy, or the like, wherein an individual is subjected to medical aid with the object of improving the individual's condition, quality of life, or prognostic outlook. In other embodiments, the term "treatment" or "therapeutic effect" also includes providing therapy to an individual that results in a decrease in tumor mass size, a reduction in the number of cancerous cells, or causing the remission of the treated tumor, cancer, or malignancy in the individual.

The subject invention provides methods for the stimulation, suppression, or modulation of the immune system of an individual comprising the administration of compositions comprising amended microbial cells (ARCs) containing cytokines and/or chemokines (e.g., those set forth in Tables 1, 8, and 9) expressed according to the teachings of the subject the invention. In one specific embodiment, the subject invention provides for the activation or stimulation of macrophage in an individual comprising the administration of ARCs comprising one or more heterologous genes in amounts sufficient to activate or stimulate the macrophage of the individual. In a specific embodiment, ARCs comprise heterologous genes encoding IFN-γ and, optionally, IFN-α.

The subject invention also provides methods of increasing viral resistance in an individual comprising the administration of compositions comprising amended recombinant microbial cells (ARCs) containing cytokines and/or chemokines (ARCs) expressed according to the teachings of the subject the invention. In some embodiments, amended microbial cells contain cytokines such as IFN-γ. In other embodiments, the compositions contain cytokines and/or chemokines that modulate a desired biologic effect. Such compositions are administered in amounts effective to stimulate, suppress, modulate, or effect a desired biological affect (e.g., antiviral activity or other activity as set forth in Table 1, 8, or 9). Thus, the subject invention also provides methods of inducing desired biological effects, such as those set forth in Tables 1, 8, and 9, comprising the administration of ARC compositions (e.g., ARCs containing heterologous genes encoding cytokines and/or chemokines that induce the desired biological effect) in amounts sufficient to induce the desired biological effect.

The subject invention also provides methods of inducing at least one desired biological effect in an individual comprising the administration of ARCs comprising one or more heterologous gene, or compositions of ARCs, in amounts effective to induce the desired biological effect. The biological effects of exemplified cytokines and/or chemokines are known to the skilled artisan and non-limiting examples of biological function associated with various cytokines and/or chemokines are set forth in Tables 8-9.

The subject invention also provides methods having both human and veterinary utility. The term "individual" includes fishes, avians, mammals, and/or reptiles. Mammalian species which benefit from the disclosed methods include, and are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans. Fish include, and are not limited to, squids, calamari, eel, octopi, cod, tuna, salmon, hake, rays, trout, haddock, halibut, plaice, whitebait, blowfish, pufferfish, pike, grouper, turbot, carp, bass, pike, sunfish, tilapia, carp, catfish, goldfish, minnow, koi, perch, mackerel, kipper, piranha, angelfish, clownfish, monkfish, coley, ling, flying fish, swordfish, suckerfish, lamprey, manta ray, sting ray, salmon, skate, herring, guppy, bloater, stickleback, whiting, bass, chub, weaverfish, spiderfish, smelt, blenney, sprat, lungfish, mudskipper, coelacanth, dab, dover sole, keogh, lemon sole, brill, roker, red snapper, gurnard, pollock, anglerfish, parrotfish, triggerfish, neon tetra, barracuda, stonefish, scorpionfish, wrasse, tench, roach, marlin, sawfish, sailfish, bluefin, anchovy, sturgeon, stoneloach, remora, barble, greyling, flounder, barramundi, shebunkin, fighting fish, garfish, pipefish, lionfish, conger eel, moray eel, sunfish, scissorfish, zander, zebrafish, mullet, sardine, whitefish, pilotfish, goby, clingfish, devilfish, john dory. Also included are sharks, including but not limited to, mako, great white, hammerhead, blue, thresher, wobbegong, lemon, whitetip, whitetip reef, gray reef, bull, sand, nurse, whale, basking, leopard, tiger, porbeagle, megamouth, tope, angel, sleeper, lantern, swell, dogfish, elfin, sand tiger, sharpnosed, black fin reef, blacknosed, bullhead, blacktip, bonnet, brown, carpet, dusky, frilled, galapagos, cookie cutter, crocodile, goblin, smoothhound, marbled cat, roundnosed, saw, seven-gilled, shovelhead, silky, smalltail, spiny dogfish, zambesi, cat, Port Jackson, whaler. Non-limiting examples of reptiles suitable for use in the instant invention include, and are not limited to, crocodiles, alligators, snakes, frogs, and turtles (such as snapping turtles and sea turtles).

Additional reptiles and/or fish include those listed in the Regulatory Fish Encyclopedia, U.S. Food & Drug Administration, Seafood Products Research Center, Center for Food Safety & Applied Nutrition; The 2001 Seafood List, U.S. Food & Drug Administration, Center for Food Safety & Applied Nutrition; Catalog of Fishes, William N. Eschmeyer, Ed., California Academy of Sciences, San Francisco, 1998; and the Encyclopedia Of Reptiles & Amphibians, Second edition, Harold G. Cogger and Richard G. Zweifel (Editors), 1998, Academic Press, San Diego, Calif. Each of these listings of reptiles and fish are hereby incorporated by reference in their entireties.

In various embodiments, compositions according to the subject invention can be administered orally, parenterally, as sprays (including inhalation sprays), topically, rectally, nasally, buccally, vaginally or via an implanted reservoir. The term parenteral, as used herein, includes subcutaneous, intradermal, intravenous, intrastriatial, intramuscular, intraperitoneal, intrathecal, intraventricular, intrasternal, or intracranial injection and infusion techniques.

Thus, the subject invention can be used as a means to treat shipping fever in animals (such as cows) or to protect the newborn calves from viral disease and/or bacterial gastroenteritis. The method is also applicable in curtailing various stress-related diseases, and for enhancing, as an adjuvant, both oral and IM/SQ human vaccinations. In either embodiment, isolated ARCs or ARC compositions comprising one or more cytokine and/or chemokine are administered in amounts effective to reduce the severity of disease or disease symptoms and/or prevent the onset of disease or disease symptoms. In certain embodiments, the ARCs contain IFN-γ.

Thus, the subject invention provides a number of non-limiting embodiments and aspects that include:

A) An amended recombinant cell (ARC) comprising one or more heterologous genes encoding a chemokines and/or a cytokine;

B) The ARC according to embodiment A, wherein the heterologous gene(s) encode(s) IL-1, IL-2, IL-3, IL-4, IL-5, IL-6, IL-7, IL-8, IL-9, IL-10, IL-11, IL-15, 1'-16, 11-18, IL-23, IL-24, erythropoietin, G-CSF, M-CSF, platelet derived growth factor (PDGF), MSF, FLT-3 ligand, EGF, fibroblast growth factor (FGF; e.g, aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-γ, IFN-α, IFN-β); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1), or chemokines (such as, but not limited to, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF 1a, TARC, or TECK) or those cytokines and/or chemokines provided in Tables 1, 8 and 9;

C) The ARC according to any previous embodiment, wherein the heterologous gene encodes IFN-γ (e.g., bovine, avian (e.g., chicken), fish, or human IFN-γ);

D) The ARC according to any previous embodiment, wherein the ARC further comprises a heterologous gene encoding IFN-α (e.g., bovine, avian (e.g., chicken), fish, or human IFN-α);

E) The ARC according to any previous embodiment, further comprising one or more heterologous genes encoding autoantigens, tumor antigens, MMR vaccines, polio vaccines, tetanus vaccines, antigens associated with pathogens normally encountered by an individual in the environment (e.g., food borne pathogens such as Klebsiella, Salmonella, Escherichia spp., hepatitis viruses, influenza viruses, etc.), pathogenic substances or antigens that may be specifically introduced into the environment of the individual, such as a biotoxin (e.g., mycotoxins, such as trichothecene mycotoxin (T-2), Staphylococcal enterotoxin B, ricin, or Clostridium botulinum neurotoxin, antigens associated with weaponized microbial cells (e.g., viruses containing toxin DNA or RNA inserts, or bacterial or fungal cells transformed with toxins [e.g., mycotoxins, such as trichothecene mycotoxin (T-2), Staphylococcal enterotoxin B, ricin, or Clostridium botulinum neurotoxin], viral pathogens or antigens thereof, fungal pathogens or antigens thereof, or bacterial pathogens or antigens thereof(e.g, smallpox, anthrax, Ebola virus, Yersinia pestis), or immunomodulatory proteins, such as superantigens, serum albumins, or protein stabilizers.;

F) The ARC according to any preceding embodiment, wherein the ARC comprises a single heterologous gene (e.g., a single cytokine, chemokine, or protein);

G) The ARC according to any preceding embodiment, wherein the heterologous gene(s) are contained in a single vector;

H) The ARC according to embodiments A through F, wherein the heterologous genes are contained in multiple vectors;

I) The ARC according to any preceding embodiment, wherein the microbial cell is Gram positive, Gram negative organisms, or a lower eukaryote, such as fungi;

J) The ARC according to any preceding embodiment, wherein the amended recombinant cells are: a) bacteria of the genera: 1) Enterobacteriaceae, including the species of the genera Escherichia, Erwinia, Shigella, Salmonella, and Proteus; 2) Bacillaceae; 3) Rhizobiaceae, such as Rhizobium; 4) Spirillaceae, such as photobacterium, Zymomonas, Serratia, Aeromonas, Vibrio, Desulfovibrio, Spirillum; 6) Lactobacillaceae; 7) Pseudomonadaceae, such as Pseudomonas and Acetobacter; 8) Azotobacteraceae and Nitrobacteraceae; or b) lower eukaryotes or fungi, such as Phycomycetes and Ascomycetes, which includes yeast, such as Saccharomyces and Schizosaccharomyces; and Basidiomycetes yeast, such as Rhodotorula, Aureobasidium, Sporobolomyces;

K) The ARC according to embodiments A-J, wherein the microbial cell is Pseudomonas fluorescens;

L) A composition an ARC comprising one or more heterologous genes encoding a chemokine and/or a cytokine according to any preceding embodiment and a carrier;

M) A method of inducing and/or accelerating an immune response in an individual to an antigen or immunogen comprising the steps of administering, to an individual (such as an avian, amphibian, reptilian, shellfish, fish, or mammalian individual):
  a) an amended recombinant cell (ARC) comprising one or more heterologous genes encoding a chemokines and/or a cytokine;
  b) a composition comprising amended recombinant cells (ARCs) comprising one or more heterologous genes encoding a chemokines and/or a cytokine; or
  c) an ARC according to embodiments A through L; and
  d) optionally, an antigen of interest; and
  e) optionally, lipopolysaccharide (LPS) in an amount effective to engender an immune response;

N) The method according to embodiment M, wherein the ARCs co-express: a) one or more antigen of interest, and b) one or more cytokine/chemokine, such as INF-γ or other cytokines/chemokines set forth in Tables 1, 8, and 9;

O) A method of accelerating the immune response of an individual to an antigen or immunogen comprising the administration of:
  a) an amended recombinant cell (ARC) comprising one or more heterologous genes encoding a chemokines and/or a cytokine;
  b) a composition comprising amended recombinant cells (ARCs) comprising one or more heterologous genes encoding a chemokines and/or a cytokine; or
  c) an ARC according to embodiments A through L; to an individual in amounts effective to accelerate the immune response of the individual;

P) A method of accelerating the development of various classes and subclasses of antibodies (e.g., IgM, IgG, IgA, and/or IgE) in an individual and to an antigen or immunogen comprising the administration of:

a) an amended recombinant cell (ARC) comprising one or more heterologous genes encoding a chemokines and/or a cytokine;
b) a composition comprising amended recombinant cells (ARCs) comprising one or more heterologous genes encoding a chemokines and/or a cytokine; or
c) an ARC according to embodiments A through L; to an individual in amounts effective to accelerate the development of a class of antibodies is the individual;

Q) The method according to embodiments M through P, further comprising the administration of an antigen or immunogen prior to, concurrent with, or subsequent to the administration of an ARC composition;

R) The method according to embodiments M through Q, wherein the ARC or ARC composition comprises IFN-γ;

S) The method according to embodiments M through Q, wherein the ARC or ARC composition comprises IFN-α and IFN-γ;

T) The method according to embodiments R through S, wherein the IFN-γ is of human, avian (e.g., chicken), bovine, or fish origin;

U) The method according to embodiments R through S, wherein the IFN-α and IFN-γ are of human, avian (e.g., chicken), bovine, or fish origin;

V) The method according to embodiments M through U, wherein the ARC or ARC composition is expressing one or more cytokine and/or chemokine are administered to an individual within two to one hundred and sixty-eight hours after exposure to an antigen or immunogen;

W) The method according to embodiments M through V, wherein the antigen or immunogen is a pathogen normally encountered by an individual in the environment or pathogenic substances specifically introduced into the environment of the individual;

X) The method according to embodiments M through W, wherein the antigen or immunogen are selected from the group consisting of autoantigens, tumor antigens, MMR vaccines, polio vaccines, tetanus vaccines, pathogens, or antigens thereof, normally encountered by an individual in the environment (e.g., food borne pathogens such as *Klebsiella, Salmonella, Escherichia* spp., hepatitis viruses, influenza viruses, etc.), pathogenic substances or antigens thereof that may be specifically introduced into the environment of the individual, such as a biotoxin (e.g., mycotoxins, such as trichothecene mycotoxin (T-2), Staphylococcal enterotoxin B, ricin, or *Clostridium botulinum* neurotoxin, weaponized microbial cells, or antigens thereof, (e.g., viruses containing toxin DNA or RNA inserts, or bacterial or fungal cells transformed with toxins [e.g., mycotoxins, such as trichothecene mycotoxin (T-2), Staphylococcal enterotoxin B, ricin, or *Clostridium botulinum* neurotoxin], viral pathogens or antigens thereof, fungal pathogens or antigens thereof, or bacterial pathogens or antigens thereof (e.g., smallpox, anthrax, Ebola virus, *Yersinia pestis*), or immunomodulatory proteins, such as superantigens, serum albumins, or protein stabilizers.;

Y) The method according to embodiments M though X, wherein the ARC or ARC composition comprises IFN-γ, and, optionally, IFN-α, and optionally, LPS;

Z) The method according embodiments M though Y, wherein the ARC or ARC composition further comprises other proteins, cytokines, and/or chemokines in addition to IFN-γ;

AA) The method according to embodiments M through Z, wherein the other proteins, cytokines, and/or chemokines are co-expressed with IFN-γ;

BB) The method according to embodiments M through AA, wherein the other proteins, cytokines, and/or chemokines are added to an ARC, or ARC composition comprising IFN-γ;

CC) Another embodiment provides methods of treating tumors, cancers, or malignancies comprising the administration of:
a) an amended recombinant cell (ARC) comprising one or more heterologous genes encoding a chemokines and/or a cytokine;
b) a composition comprising amended recombinant cells (ARCs) comprising one or more heterologous genes encoding a chemokines and/or a cytokine; or
c) an ARC according to embodiments A through L; to an individual in amounts effective to treat tumors, cancers, or malignancies;

DD) The method according to embodiment CC, further comprising the administration of chemotherapeutic agents and, optionally, tumor/cancer antigens;

EE) The subject invention also provides methods for the of inducing a desired biological effect in an individual comprising the administration of:
a) an amended recombinant cell (ARC) comprising one or more heterologous genes encoding a chemokines and/or a cytokine;
b) a composition comprising amended recombinant cells (ARCs) comprising one or more heterologous genes encoding a chemokines and/or a cytokine; or
c) an ARC according to embodiments A through L; to the individual;

FF) In one aspect of embodiment EE, the desired biological effect is selected from the group consisting of: 1) activation or stimulation of macrophage in an individual; 2) stimulation, suppression, or modulation of the immune system of an individual; 3) increasing viral resistance in an individual; and 4) effect a desired biological affect as set forth in Table 1, 8, or 9);

GG) In yet another embodiment, the subject invention can be used as a means to treat shipping fever in animals (such as cows) or to protect the newborn calves from viral disease and/or bacterial gastroenteritis. The method is also applicable in curtailing various stress-related diseases, and for enhancing, as an adjuvant, both oral and IM/SQ vaccinations in individual (such as humans). In either embodiment, isolated ARCs or ARC compositions are administered in amounts effective to reduce the severity of disease or disease symptoms and/or prevent the onset of disease or disease symptoms. In some embodiments, ARCs contain cytokines such as IFN-γ;

HH) In various implementations of the methods of embodiments M through GG, compositions according to the subject invention can be administered orally, parenterally, as sprays (including inhalation sprays), topically, rectally, nasally, buccally, vaginally or via an implanted reservoir. The term parenteral, as used herein, includes subcutaneous, intradermal, intravenous, intrastriatial, intramuscular, intraperitoneal, intrathecal, intraventricular, intrasternal, or intracranial injection and other infusion techniques;

II) The subject invention also provides methods of making an amended recombinant cell (ARC) comprising a) one or more heterologous genes encoding a chemokines and/or a cytokine or b) an ARC according to embodiments A through L comprising the introduction of one or more heterologous genes into a cell. The cell may be grown in any convenient nutrient medium, where the DNA construct provides a selective advantage (e.g., growth in a selective medium containing antibiotics), providing for a selective medium so that substantially all or all of the cells retain the heterologous gene(s). These cells may then be harvested in accordance with conventional ways and modified in the various manners described above. Alternatively, the cells can be fixed prior to harvesting; and JJ) In one aspect of embodiment II, various techniques for inactivating and amending the host cells can be use that include acidification with acids such as acetic acid, with or without the addition of a halogen, such as iodine; UV irradiation; lyophilization; toxins, e.g., antibiotics; phenols; anilides, e.g., carbanilide and salicylanilide; hydroxyurea; quaternary alcohols; antibacterial dyes; EDTA and amidines; non-specific organic and inorganic chemicals, such as halogenating agents, e.g., chlorinating, brominating or iodinating agents; aldehydes, e.g., glutaraldehyde or formaldehyde; toxic gases, such as ozone and ethylene oxide peroxide; psoralens; desiccating agents; or the like, which may be used individually or in combination. Alternatively, the methods set forth in paragraphs 31, 32, 33, and/or 34, supra, may be used. Compositions can also be formulated in any carriers, including for example, carriers described in E. W. Martin's *Remington's Pharmaceutical Science*, Mack Publishing Company, Easton, Pa.

The terms "comprising", "consisting of" and "consisting essentially of" are defined according to their standard meaning. The terms may be substituted for one another throughout the instant application in order to attach the specific meaning associated with each term. Likewise, the term "about" can be substituted with the phrase "at least about" and the term "containing" can be substituted with the term "comprising" throughout the subject application.

Following are examples illustrating procedures for practicing the invention. These examples should not be construed to be limiting; but should include obvious variations of the subject invention. Unless noted otherwise, solvent mixture proportions are by volume and percentages are by weight.

EXAMPLE 1

*Pseudomonas fluorescens* Host Cells and Expression Systems

Figure 1:
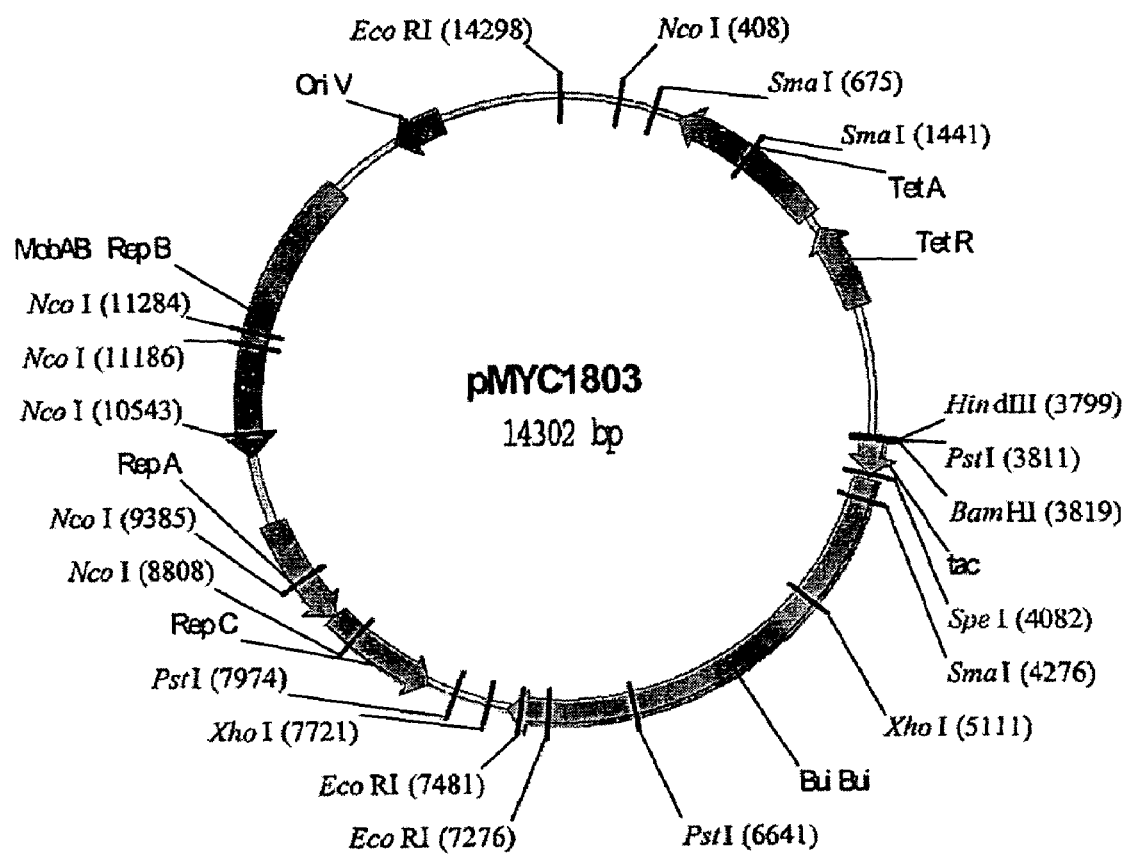
Figure 3:
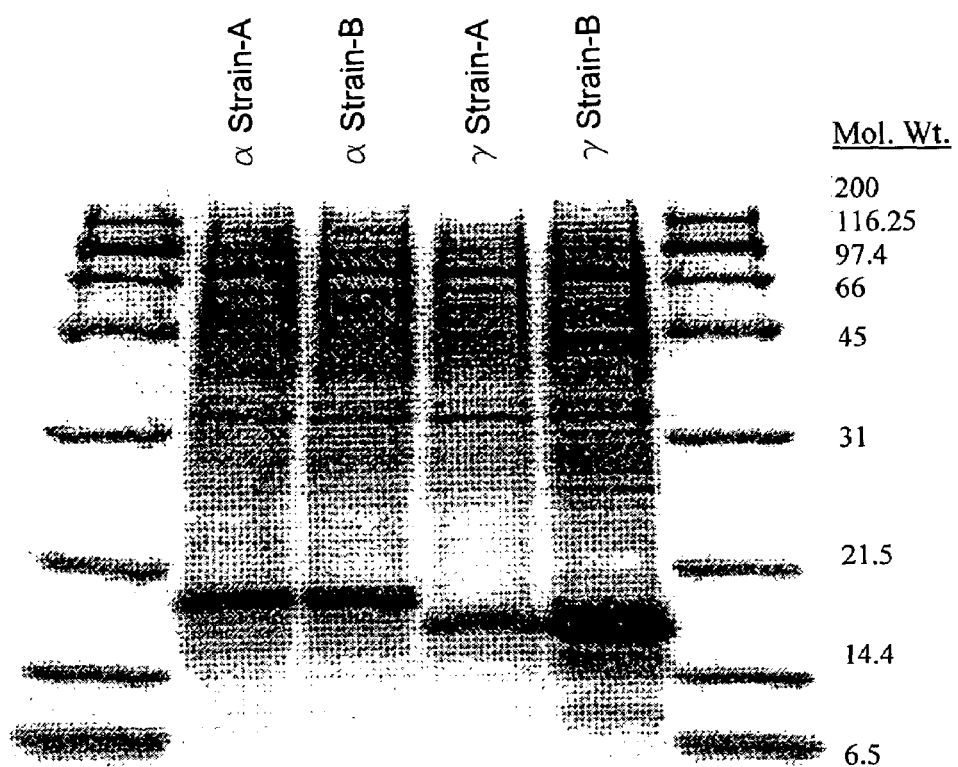
Figure 4:
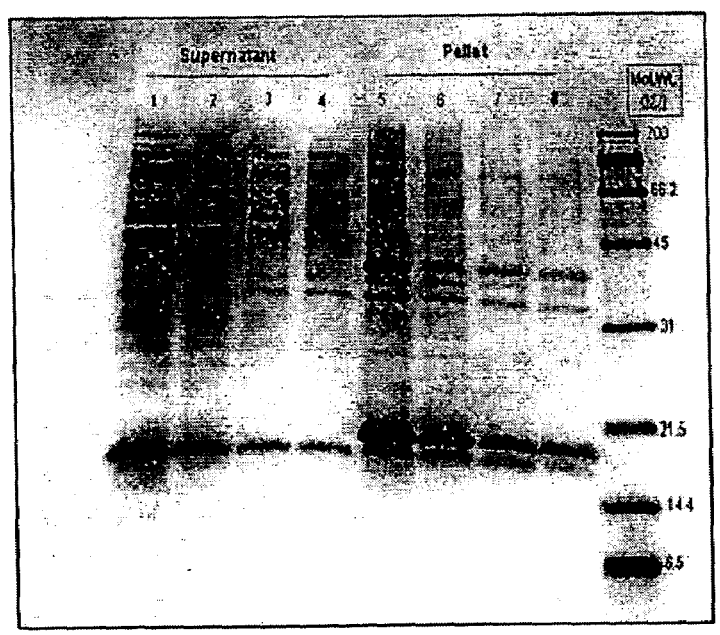

Production strain MB324 was used for transformation experiments and plasmid pMYC1803 (FIG. 1) was used for subcloning experiments. The *Bacillus thuringiensis* BuiBui insert of the vector was excised with restriction enzymes SpeI and XhoI prior to insertion of the bovine IFN-γ (BGI) gene or chicken IFN-γ (CGI) gene. The published nucleotide sequences of BGI (FIG. 2) and CGI were obtained from GenBank using SeqWeb software. The sequence to be synthesized was modified to exclude the signal sequence and include ribosome binding, SpeI and XhoI restriction sites. The resulting sequence information was sent to Operon Technologies for gene synthesis. Sequencing of the cloned gene was done with a P.E. 377 sequencer and analyzed with Factura and AutoAssembler software. The forward and reverse primers used for sequencing were made by Genosys.

EXAMPLE 2

Subcloning of Interferon Genes

Conical tubes (50 mL) containing 5-mL L-broth (LB) were inoculated with ice chips from frozen glycerol stock cultures of *P. fluorescens* MB324. The cultures were incubated in a rotary shaker overnight at 300 rpm and 30° C. 0.75 mL from each culture was used to inoculate 50 mL of LB in 250-mL side-baffled flasks. The cultures were shaken for two hours at 300 rpm and 30° C. and grown to an A600 (absorbance at 600 nM) of 0.2 to 0.3. Cultures were then cooled on ice and pelleted by centrifugation at 3000 rpm. Pelleted materials was washed with cold, sterile, distilled water three times and the pellets were re-suspended in water.

The cell suspensions (about 100 µL each) were added to electroporation cuvettes, mixed with 10 µL of either interferon gene or control ligation mixtures; re-suspended cells were electroporated with a BioRad GenePulser in 0.2 cm cuvettes at 200 ohms, 25 µF and 2.25 kV and "pulsed" at time-constants between 4.6 and 4.8.

One-mL of LB was added to each sample, and the liquid was transferred to iced 2059 Falcon tubes. The tubes were loosely capped, shaken for two hours at 280 rpm and 30° C. 100 µL to 200 µL aliquots were plated on L-broth-tetracycline (LB-tetracycline) (30 µg/mL) agar and incubated at 30° C. overnight. One colony from each of two 100 µL platings and two colonies from a 200 µL plating were randomly selected and used to inoculate 50 mL conical tubes with LB-tetracycline broth, as described above. Samples of the resulting cultures were mixed with sterile glycerol (1.0 mL culture plus 0.25 mL 75% glycerol) and stored at −70° C. The remaining culture (1.8 mL) was centrifuged for 10 minutes in a 2 mL Eppendorf tube. The pellets were re-suspended in 0.5 mL of Qiagen P1 solution, followed by gentle inversion six-times with 0.5 mL P2 solution.

Within about five minutes, the sample was re-inverted six times with N3 solution and iced. The chilled sample was centrifuged for ten minutes, carefully separated from the pellet and surface scum, and the resulting supernatant liquid (about 1.5 mL) was transferred to a fresh Eppendorf tube. The sample was further purified with a Qiagen spin column and collection tube by spin-loading the entire 1.5 mL sample onto the column with two, 30 second, 14000 RPM (14 K) spins of about 0.7 mL to 0.8 mL aliquots. The spin-column was washed with 0.62 mL Qiagen PB and 0.85 mL PE, with a final spin of 90 seconds. The column was transferred to a new Eppendorf tube, eluted for 1 minute with 50 µL Tris-EDTA, and spun for one minute at 14 K. The eluent was transferred to a new Eppendorf tube and stored at −20° C. The resulting mini-preps were digested with XhoI and SpeI and analyzed by agarose-gel electrophoresis.

EXAMPLE 3

Expression and Quantitation of Interferon Protein

Based on mini-prep results, one clone of MR324 with an IFN-γ insert was selected for expression analysis. *P. fluorescens* strains MR843 and MR837 were used as interferon-negative controls. LB-tetracycline seed-flasks were grown to A600 0.15 to 0.5 and normalized to 0.15 for 2% dilution into 1-liter shake flasks containing 200-mL tetracycline production medium. *P. fluorescens* cells were grown to approximately A600 0.4 at 30° C. with rotary shaking for 24 hours. The cells were induced with 0.6 mL of 100 mM IPTG+5 mL 40% MSG for an additional 48 hours. The cells were examined microscopically for general appearance and inclusion body formation.

Fifty-mL samples were taken and stored at 4° C. in conical tubes for analysis of expression by sodium dodecyl-sulfate polyacrylamide-gel electrophoresis (SDS PAGE.) A total of 100 µL was centrifuged for five minutes at 14 K to pellet the cells. Pellets were re-suspended in 100 µL 1×Laemmli buffer and boiled for 3 minutes, and supernatant samples were diluted 1:1 with Laemmli buffer prior to being boiled. Ten μL of boiled sample were mixed with 30 μL of fresh Laemmli buffer and boiled for an additional 3-minutes. The preparations were frozen overnight, thawed the following day, heated to 70° C. for five minutes, loaded (10 μL each) into the wells of a 12-lane, 15% BioRad gel, and electrophoresed with BioRad running buffer. The electrophoresis ran for 20 minutes at 50 volts followed by 1 hour 20-minutes at 75 volts. After the run, the gels were washed in distilled water three times for five minutes each and stained with BioRad's BioSafe stain for 1.5 hours. The stained gels were de-stained in distilled water with one change after one hour. Quantitation was accomplished with an MD densitometer by comparing the Coomassie Blue intensity of the samples to interferon-minus controls and a BSA protein standard.

Replacement of the BuiBui toxin gene with the BGI gene at the SpeI and XhoI sites of pMYC1803 occurred smoothly (FIG. 1). Similar results were obtained for the subcloning of the CGI gene. All the transformants selected had the desired interferon insert, as verified first by agarose-gel electrophoresis, and then by sequencing the inserted DNA (FIG. 2). One clone of the DnaK, chaperonin containing strain of *P. fluorescens*, MB324, was selected for further study.

A major band of protein was observed at the molecular weight expected for BGI and CGI (for example see FIG. 3) and expression of both BGI and CGI in *Pseudomonas* was about 40% of total cellular protein. Identity of the major band with authentic BGI or CGI was confirmed by purification of the protein contained in the major band, coupled with bioassays of the purified product. With the optimization of expression and high-density fermentation achievable with Pseudomonas, interferon production of greater than 1000 Kg can be attained in a single fermentation production run.

EXAMPLE 4

Solubility Assay

A 0.975 mL volume of *P. fluorescens* culture was centrifuged in a microfuge for 5 minutes at 14,000 RPM. The supernatant liquid was decanted and the cells were resuspended in lysis buffer up to the starting volume. [Lysis buffer: Tris HCl, 50 mM, pH 7.5 final; NaCl, 200 mM; glycerol, 5% v/v; EDTA, 20 mM; Triton X-100, 5% v/v; and, added last, DTT, 1 mM] Screw-cap microfuge tubes (2 mL) were filled about ¾ full with 0.1 mm glass beads and topped off with cell suspension. The tubes were given a quick shake to mix the beads and remove air bubbles, and further filled to the top with cell suspension. The tubes were capped, sealed, and inserted into a BioSpec mini bead-beater for 60 seconds at 5000 rpm. The samples were kept on ice between beatings and beat 3 to 5 times until about 90% of the cells were lysed. Cell lysis was observed by microscopic observation. A volume of 0.025 mL of the lysed cell preparation was pipetted from each tube, minus beads, into new microfuge tubes and centrifuged for 5 minutes. The supernatant fraction was carefully transferred to another tube with 0.075 mL LSB, and 0.100 mL LSB was added to the pellet fraction. The supernatant and pellet fractions were re-suspended with a Vortex stirrer, the tubes were capped, placed in a boiling water bath for five minutes, and 0.005 mL to 0.010 mL aliquots of the fractions SDS PAGE were analyzed. Assessment of expressed BGI or CGI protein solubility in *Pseudomonas*, using either a French-Press or a BioSpec Mini Bead-Beater produced equivalent results.

As shown in FIG. 4, the solubility of BGI in *Pseudomonas* cells was tested and indicated that most, if not all, of the BGI remained in soluble form. Similar results were obtained for CGI. To do these solubility-tests, viable unamended *Pseudomonas* cells were broken in a French Press (or mini-bead beater), and centrifuged to separate cell debris and any inclusion bodies from soluble proteins. SDS gels of these two fractions indicated that BGI was retained in the soluble portion, whereas BAI (bovine α-interferon), a marker in this example that had been cloned and expressed for another experiment, occurred primarily in the insoluble fraction. Furthermore, unlike BGI (or CGI), BAI formed large inclusions in *Pseudomonas*, which were highly visible under phase-contrast microscopy.

SDS-PAGE analysis of French-Pressed *P. fluorescens* cultures containing both BAI and BGI are shown in FIG. 4. *Pseudomonas* cells were ruptured in a French Press and centrifuged at 16000 g for five minutes. Lanes 1-4 are supernatant samples showing a single, major band (about 17 kDa) of soluble BGI with no BAI visible. Lanes 5-8 are pelleted samples showing a major band (about 18 kDa) of insoluble BAI together with small amounts of contaminating soluble BGI (lower band, about 17 kDa). The contamination appears to be due to spillover from the supernatant fraction and unlysed cells.

EXAMPLE 5

*Pseudomonas* Amended Recombinant Cell (ARC) Amendment Procedure

All materials used in this procedure were thoroughly sterilized. A completed *P. fluorescens* fermentation culture was poured into a sterile beaker containing a sterilized magnetic stirring bar. The culture was stirred slowly, while the pH was monitored with an alcohol-sterilized pH-probe. Glacial acetic acid was added, drop-wise, over about 10 minutes, until a pH of about 4.3 was reached. Following titration of the culture to about pH 4.3, concentrated Lugol iodine was added to 1% v/v. [Lugol iodine: sterile distilled water, 90 mL; KI, 10 g/100 mL; Iodine, 5 g/100 mL; glacial acetic acid, 10 mL]. The solution was stirred well and aseptically transferred to a new, sterile beaker containing a sterile stirring bar. The solution was covered and stirred for one hour at room temperature. The cells can be treated for longer periods of time (e.g., up to two hours) with similar results. The Lugol/cell mixture was transferred to a sterile 500 mL capped bottle and centrifuged at 7500 rpm for 15 minutes. The supernatant liquid was decanted and discarded. Sterile distilled water at room temperature was added up to the original volume, the pellet was dislodged with a sterile spatula, and the cells were re-suspended with an autoclave-sterilized, IKA, Ultra-Turrax, T25 homogenizer for about 10 seconds at #2 setting. Resuspension and centrifugation were repeated, as described above, three times to wash the cells free of Lugol solution. During the final wash the ARC cells were resuspended to 1/10 original volume and, frozen at −80° C. in sterile screw-cap tubes for long-term storage. Samples of 0.1 to 1.0 mL were plated on L-broth and LB-tetracycline to verify that there were no live cells.

EXAMPLE 6

Quantitation of Interferon Bioactivity

For in vitro bioassays, bovine kidney (MDBK) cells were grown to confluence, and incubated with control *Pseudomo-*

*nas* samples and with various dilutions of BGI/ARC samples for 24 hours. All plates were then challenged with vesicular stomatitis virus (VSV) and incubated for an additional 24-hour period (10 and 29-32).

Microtiter plates were made confluent with bovine kidney (MDBK) cells. The supernatant liquid was discarded and 100 µL of MEM plus 5% FBS was added to each well. Samples, 100 µL each, were added to the top row in two columns. For the interferon-positive control an initial concentration of 100 U/mL was used. The specific activity of standard BGI was $3\times10^6$ U/mg. Serial dilutions at 1:2 started in row one and proceed to the bottom of the plate. The microtiter plates were incubated at 37° C. overnight to allow any interferon in the samples to induce an antiviral state in the MDBK cells. The following day, a stock of VSV was diluted in MEM to obtain about 50 plaque-forming units (PFU) per 100 µL. Diluted virus, 100 µL, was added to each well after all the liquid was removed from the plates. The plates were incubated at 37° C. for one hour to allow VSV to infect the MDBK cells. The virus inoculum was then removed from the plates. One drop of methylcellulose was added from a 10 mL pipette to each well. The plates were incubated once again overnight at 37° C., following which the methylcellulose was removed and the plates were stained with crystal violet for about five minutes.

The initial experiments were surprising with respect to the outstanding antiviral effects of BGI/ARC cells. Fixed, intact cells, containing (BGI/ARCs), gave the best results with titers between $10^7$ and $10^{8.5}$. At the high level of dilution necessary to protect 50% of the kidney cells from death due to VSV infection only tens of picograms of BGI/ARC were required for activity. In contrast, bovine IFN-α (BAI) in recombinant amended cells was considerably less active (Table 2).

As illustrated in Table 3, subsequent similar in vitro experiments confirmed the efficacy of BGI/ARCs with respect to their ability to protect bovine kidney cells from VSV.

The low activity of BAI co-expressed with BGI in ARCs (note: even though it's activity is low, BAI does synergize with BGI, stimulating BGI's activity by 10 fold, cf Table 2) appears to be due to the observed aggregation of much of the BAI protein in *Pseudomonas* as an insoluble inclusion body. Recent results with groEL/groES chaperonins and fusion proteins for solubilizing inclusion bodies in *E. coli* or other expression systems suggest that these or other chaperonins may be useful for maintaining BAI intracellularly in a soluble, active form. However, the dnaK chaperonin strain, MB324, which was used in the present study, appeared to be only slightly effective for BAI in this regard.

EXAMPLE 7

BGI/ARC Stability

Samples of BGI/ARCs (in sterile water) were taken from storage at −80° C. and held over a six-month period at −20° C., 4° C., room temperature (RT), and 37° C. to test shelf-life stability; no manipulation of the samples occurred nor were any additional materials added to the samples. The samples were returned to −80° C. after various incubation times and stored until completion of the six-month test period. Bioassays, utilizing the bovine-kidney-cell—VSV challenge assay, of the BGI/ARC samples showed no loss of activity over six months storage at −20° C. or 4° C. Furthermore, BGI/ARC samples remained stable for eight to seventeen days at room temperature and BGI/ARCs can remain stable for up to four days at 37° C. (see FIG. 5).

Both the amount and the activity of BGI in fixed *Pseudomonas* cells were extremely high. As illustrated in the foregoing examples: 1.) *Pseudomonas* is a good biofactory for IFN-γ, capable of producing up to 40% or more of total cell-protein as interferon; 2.) The ARC stabilization and amendment procedures do not appreciably damage IFN-γ nor do they produce a barrier to expressed IFN-γ contents; 3) BGI/ARCs are active in the picogram range; 5.) BGI/ARCs have excellent microparticle-flow, syringe handling, and suspension properties; 6.) The preparation of fixed ARC protects BGI and other expressed protein products from denaturation from repeated handling, freezing, or other potentially damaging manipulations.

In mammals, activated T-cells and natural killer cells can be stimulated by alloantigens, tumors, or mitogens to produce γ-interferon. In addition to γ-interferon's antiviral activity, it has been shown to inhibit tumors (10-12) and promote terminal differentiation of B cells to immunoglobulin-producing cells(15;16). It can also activate macrophage, enhance the cytotoxicity of natural killer cells, stimulate T-cell cytotoxicity, and synergize with α-interferon (7) via specific, cell-surface receptors (17). Thus, the enhanced γ-IFN activity of BGI/ARCs makes for a very useful stand-alone therapeutic or prophylactic product, and can be additionally valuable when IFN-γ is co-expressed with other cytokines.

As evidenced in the following examples, BGI/ARCs perform even better in vivo than they do in vitro. Although other laboratories (13; 18;26) have shown IFN-γ, as well as other species-specific gamma-interferons to be extremely effective adjuvants, the enhanced activity of IFN-γ/ARCs and their already-stated advantages of stability, low cost, ease of production, time-release, non-flocculent, and microparticle flow properties make IFN-γ/ARCs an extremely attractive adjuvant alternative. Moreover, results with bovine IFN-γ/ARCs show they have the surprising capability to act as an immunoaccelerant, as well as powerful immunoadjuvant IFN-γ extracted from *P. fluorescens* was extremely active, and surprisingly, it was just as active when tested in the kidney tissue culture assay. As shown in the following examples, IFN-γ in its ARC-encapsulated form is even more active in vivo than it is in its soluble form, and has the additional surprising property of acting as a vaccine immunoaccelerant.

EXAMPLE 8

Major Histocompatability (MHC) Class II Induction Assays

Another method for assessing the activity of BGI was to measure the effect of BGI on the ability of kidney or dendritic cells to induce the production of MHC Class II antigens MDBK or dendritic cells were resuspended at $5\times10^6$ cells/mL in MEM plus 10% phosphate buffered saline. Four-mL was aliquotted into six-well plates and incubated overnight at 37° C. All of the media was removed from the plates and each well rinsed with HBSS. One half of the wells received 5 mL MEM plus 100 ng/mL BGI. The other half received MEM with BGI. The plates were incubated overnight at 37° C. Once again the media was removed and the wells rinsed with HBSS. To each well 1 mL of the following mixture was added: 17.5-mL lidocaine; 32.2-mL HBSS, pH to 7.4 with 1 N NaOH. The cells were removed from the wells with a cell scraper, washed free of lidocaine, and FACS stained and analyzed with a Becton Dickenson Facscan. (2; 3; 5; 7; 14; 15; 18; 19; 26; and 27).

In the following assays either commercial bovine kidney cells (MDBK) or dendritic cells isolated from cattle were used. The value "MHC %" refers to the percentage of cells measured expressing MHC antigen. As illustrated in Table 4, derived from FIGS. 6A and 6B, side-by-side comparison of BGI/ARCs, ARC controls, and two different purified samples of BGI was performed.

Figure 6A:
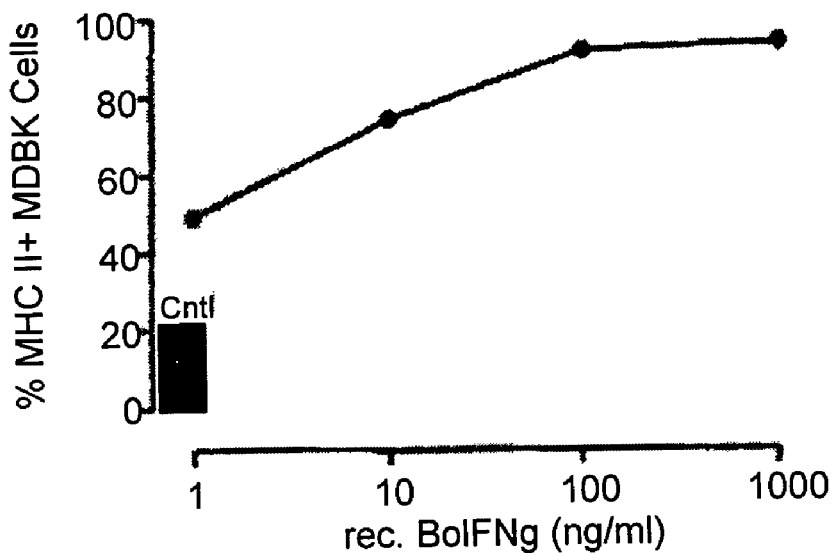
Figure 6B:
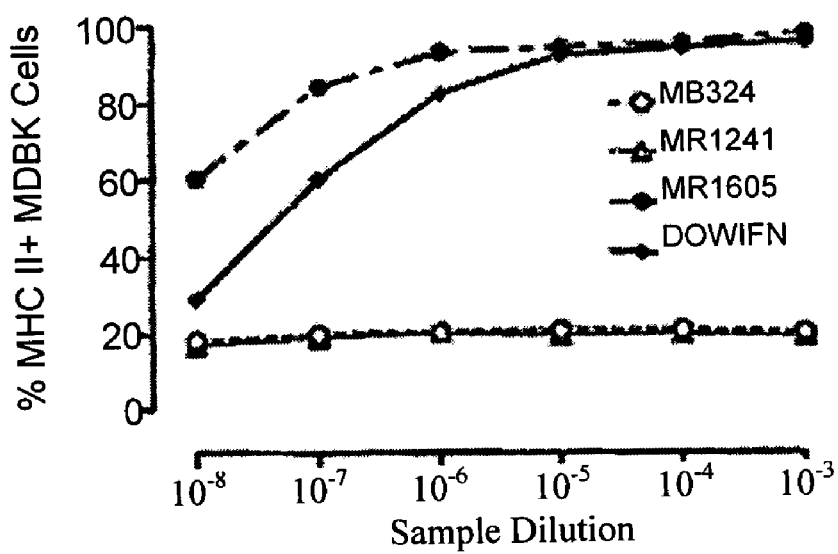

FIG. 6A is a graphical illustration of the MHC expression curve of pure recombinant bovine IFN-γ (RecBoIFNγ) from *E. coli*. FIG. 6B illustrates the comparison of 1.) untransformed *P. fluorescens* host-cell control (MB324), 2.) pMYC1803 (transformed with vector only) ARC control (MR1241),3.) BGI/ARC (transformed with BGI gene) (MR1605), and 4.) purified BGI from *P. fluorescens* (DOW-IFN). There is virtually identical expression of MB324 and MR1241.

Figure 7A:
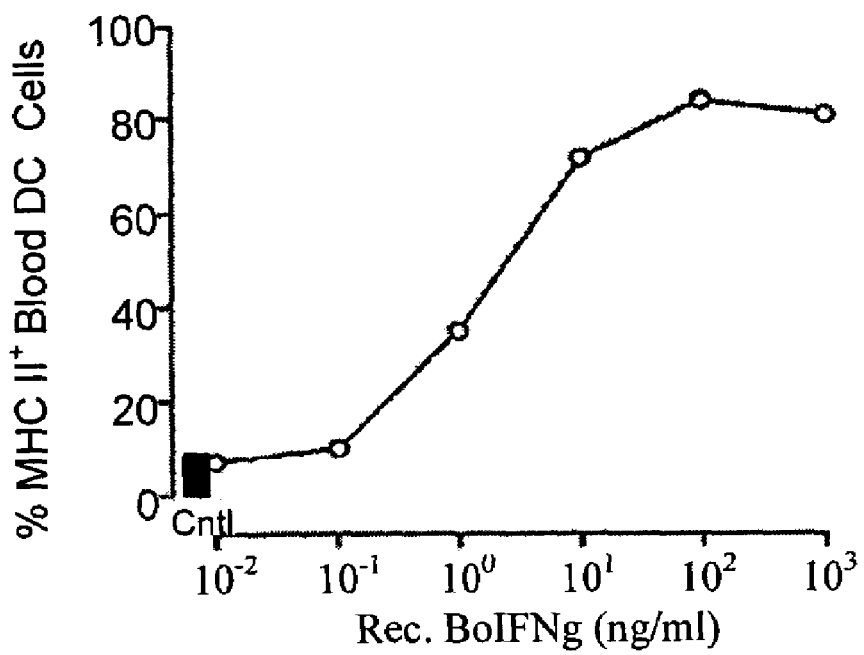
Figure 7B:
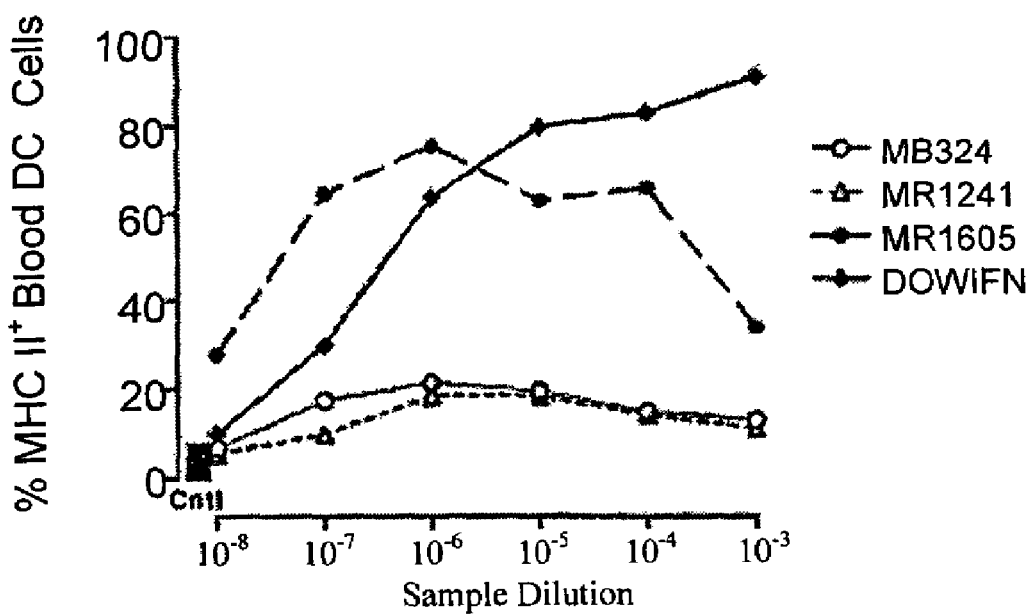

Blood-harvested dendritic cells were also assayed for MHC expression. FIG. 7A illustrates the effects of purified RecBoIFNγ from *E. coli*. FIG. 7B is a comparison of 1.) untransformed *P. fluorescens*, host-cell control (MB324), 2.) pMYC1803 (transformed with vector only) ARC control (MR1241),3.) BGI/ARC (transformed with BGI gene) (MR1605), and 4.) purified BGI from *P. fluorescens* (DOW-IFN).

EXAMPLE 9

Dose Titration of BGI activity in Cattle (2; 3; 5; 7; 14; 15; 18; 19; 26; and 27)

Four groups of cattle were tested to determine the minimum dose of bovine IFN-γ/ARC (BGI/ARC) which would display detectable biological activity. Four groups of five calves each, A, B, C, and D, were subcutaneously injected with doses of 4800, 480, 48, and 0 μg, respectively, of BGI/ARCs. The 0 μg ARC control was identical to the experimental samples except that the control *Pseudomonas* cells lacked the bovine IFN-γ gene.

The protocol used for this experiment follows:

1. Three mL of BGI/ARC and three mL of ARC control were diluted with phosphate buffered saline (PBS) to a final volume of six mL, enough to provide five equivalent one-mL doses for each of five calves, representing the high BGI concentration and ARC control groups, respectively. In addition, two serial ten-fold dilutions of the stock BGI/ARC preparation were prepared by diluting 0.4 mL BGI/ARC stock solution or the 1/10 dilution of the stock to a final volume of 4.0 mL with PBS. Three mL of each BGI/ARC serial dilution(1/10 and 1/100) were then diluted to a final volume of six-ml, enough to provide five one-ml doses for each of the two groups of calves, representing the 1/10 and 1/100-diluted BGI/ARC samples, respectively.
2. BGI/ARC and ARC control samples were dispensed into sterile, sealed glass vials and labeled with appropriate Group number (Table 5), date, and instructions for administration.
3. The samples were stored at 4° C. until administered by animal care staff.

A clinical veterinarian was provided with a list of animal numbers and their group designation. Calves were randomly assigned to experimental groups by generating a list of random numbers (Excel Program). Random numbers were ranked and sequentially assigned to Groups A, B, C, and D.

Figure 8:
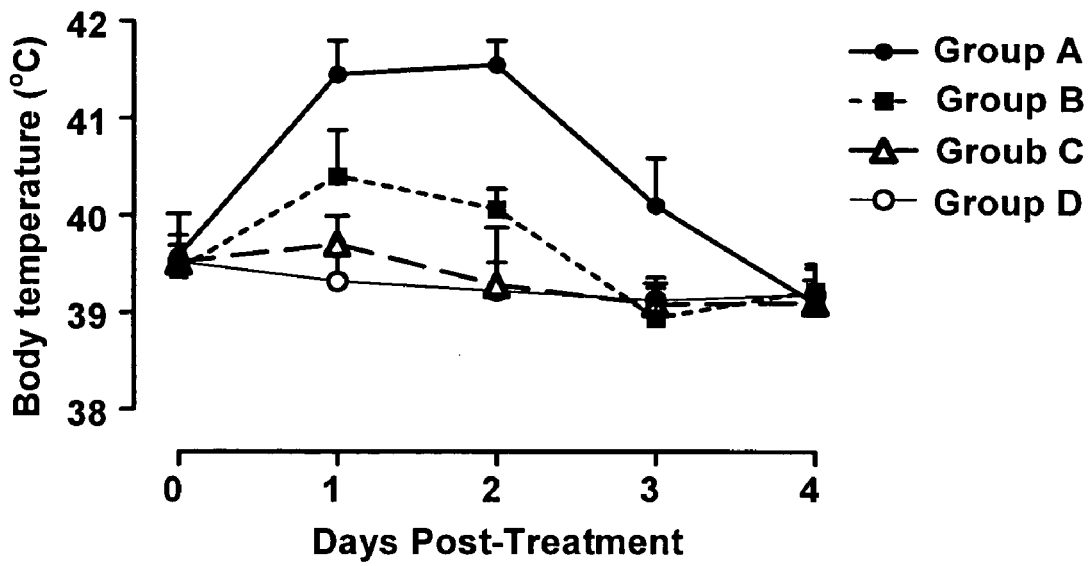
FIG. 8 shows the effects of BGI/ARCs on body temperature of tested calves
Figure 9:
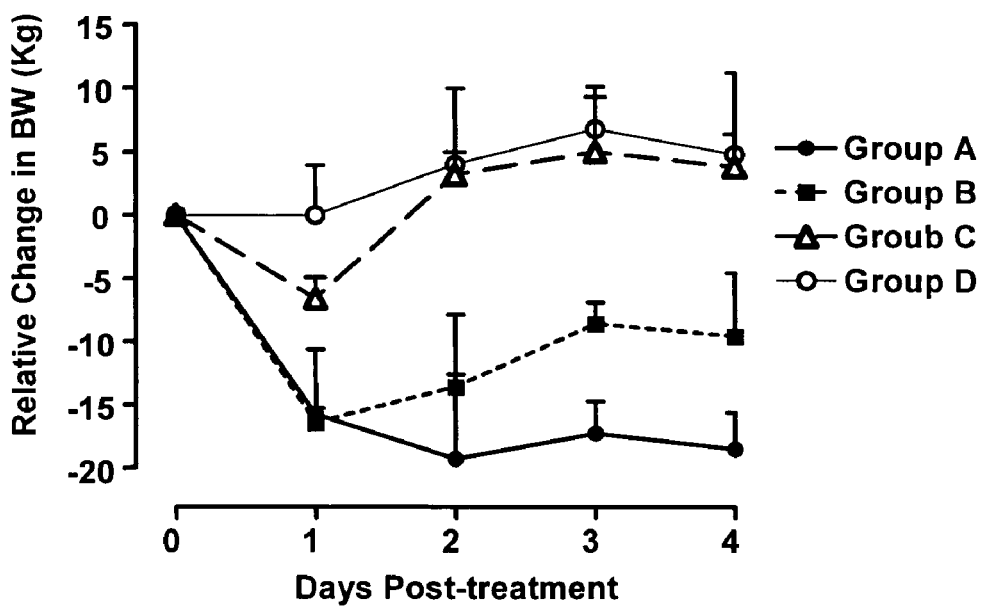
FIG. 9 depicts the effects of BGI/ARCs on body weight of tested calves

The criteria used to detect biological activity were changes in body temperature and body weight. A single subcutaneous injection of approximately 4800 μg BGI/ARC induces a significant elevation in body temperature for 48 h post-treatment (FIG. 8) and is associated with a prolonged (>4 days) decrease in body weight (FIG. 9). A single subcutaneous injection of approximately 480 μg BGI/ARC induces a mild elevation in body temperature (<1° C.) for 48 h post-treatment and is associated with a prolonged (>4 days) decrease in body weight. A single subcutaneous injection of approximately 48 μg BGI/ARC induces no detectable change in body temperature but is associated with a small (<5 kg) decrease in body weight at 24 hour post-treatment. A single subcutaneous injection of approximately 0.5 mL of an ARC control sample induces no detectable changes in body temperature or body weight.

Figure 10:
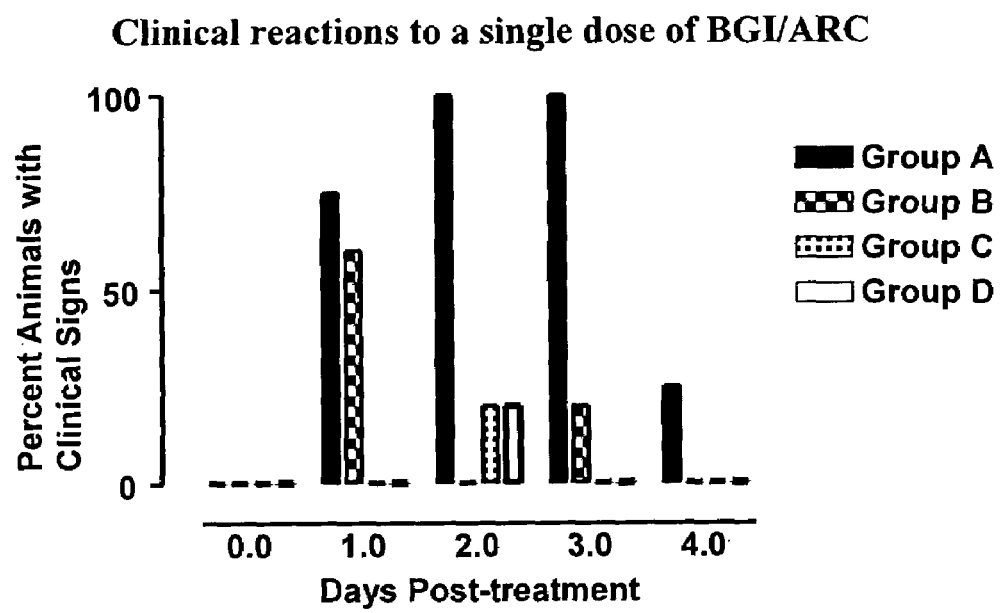
FIG. 10 depicts the effects of BGI/ARCs on bovine clinical symptoms.

One animal from Group A, at the 4800 μg BGI/ARC dose, died on Day 1 post-treatment. Post-mortem results revealed lesions consistent with a diagnosis of bloat (rumen stasis). No other gross or histological lesions were reported. The other calves in this group survived but showed typical, interferon, over-dose symptoms, including severe weight-loss and elevated body temperature. Animals were assessed daily for a variety of clinical signs, including lameness, lethargy, anorexia, diarrhea, and swelling at the injection site. The majority of Group A animals (4800 μg BGI) displayed one or more of these clinical signs on days 2, 3, and 4 post-treatment. Group B (480 μg BGI) animals also displayed a high frequency of clinical signs but only on the first day after treatment (FIG. 10). Dose titration studies indicate that the doses of BGI in BGI/ARC selected for adjuvant studies should be in the range of 50 μg or less. Animals treated with this dose of BGI should not display any clinically detectable adverse reactions. The strong, characteristic interferon reactions produced by BGI/ARCs in calves is consistent with ARC-delivered BGI having a specific activity approximately 1000 times greater than purified, soluble bovine IFN-γ.

Serum haptoglobin levels were tested in each animal at 0, 2, and 4 days post injection (Table 6). Group C cattle produced a mean average of 243,011 ng/mL of haptoglobin at a dose of 48 μg of BGI/ARC. Comparing this result to the mean average of 38,807 ng/mL of haptoglobin produced in the untreated animals indicates that a dose as low as 48 μg can induce a dramatic increase in haptoglobin production.

Serum 2'5' A synthetase levels were also measured in each animal at 0, 2, and 4 days post injection and are illustrated in Table 7.

EXAMPLE 10

Effect of BGI/ARC on the Secondary Immunization Response

Figure 11:
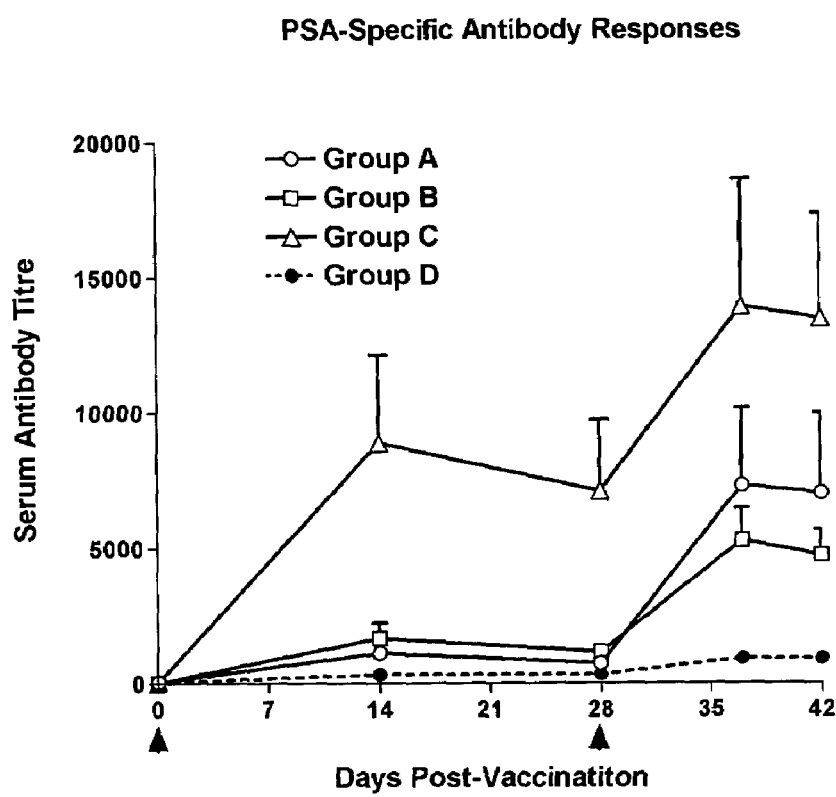
FIG. 11 illustrates the immunoadjuvant activity of BGI/ARCs and the ability of BGI-ARCs to accelerate the immune response of calves to an antigen (e.g., porcine serum albumin).

The calves were immunized with 50 μg of porcine serum albumin (PSA) in conjunction with the following treatments: Group A, 250 μg BGI/ARC; Group B, 25.0 μg BGI/ARC; Group C, 2.5 μg BGI/ARC; Group D, ARC-control (ARC lacking a BGI insert) with sufficient ARCs to provide a control equivalent in cellular mass to Group A. Calves received a primary immunization on Day 0 (arrow) and the secondary immunization on day 28 (arrow). Each group consisted of six, 6-8 month old, Angus-Hereford-cross calves that were either females or neutered males. Data presented are the mean±SEM and are illustrated in FIG. 11.

Data for the secondary immune response are consistent with data for the primary immunization. The lowest dose of BGI/ARC (2.5 μg BGI) gave the greatest enhancement of antibody titers, whereas the ARC-minus, BGI control enhanced the immune response little, if at all. The difference between the control and the maximum titer increased from 27 fold in the primary response to over 150 fold in the secondary response. As illustrated in FIG. 12, BGI/ARCs have a proliferative effect on lymphocytes (as measured by the incorporation of $^3$H thymidine).

The present examples illustrate that ARCs are valuable tools for the inexpensive production, preparation, and delivery of stabilized IFN-γ. IFN-γ/ARCs are also surprisingly useful as immunoadjuvants and accelerants of the immune response. As described herein: 1.) The *Pseudomonas fluorescens* expression system can be used to inexpensively produce prodigious amounts of active IFN-γ having an expression level equal to that obtained for a commercial insecticide, MVP(T (9), protein (the process described herein can produce more than one ton of IFN-γ from a single 100,000-liter fermentation); 2.) The chemical sterilization procedure amends the *Pseudomonas* cells, stabilizes the IFN-γ contents of ARCs, and provides for the effective release of IFN-γ within or on the surface of a macrophage or other IFN-γ reactive cell; 3.) The amended and stabilized BGI/ARCs are active in their intact form, and picogram levels of IFN-γ protect cells from infection by virus (see, for example, VSV infection of bovine kidney cells); 4.) Unlike many other recombinant proteins, IFN-γ is soluble and can be over-expressed in *P. fluorescens* in soluble form and does not form inclusion bodies in cells even when expressed at levels greater than 40% of total cell protein; 5.) BGI/ARCs have excellent shelf-life properties, remaining stable and active after several weeks at 37° C. and remain active for more than 6 months without loss of activity when frozen; 6.) BGI/ARCs have exceptional physical properties; they are mechanically durable, nonflocculant microscopic particles that can remain in suspension and easily pass through a syringe; 7.) BGI/ARCs have desirable time-release properties; 8) Microgram quantities of IFN-γ in BGI/ARCs produce an unexpectedly strong response in cattle and promote unexpectedly vigorous immunoadjuvant responses and immunoacceleration, and 9.) BGI/ARCs can be given intramuscularly, subcutaneously, or introduced to the body through mucosal membranes, making non-invasive delivery possible. The following examples using avian IFN-γ/ARCs (CGI/ARCs) further illustrate the usefulness of the subject invention.

EXAMPLE 11

Effects of IFN-γ on Avian Macrophage

Avian (chicken) macrophage cell lines (MQ-NCSU and HD 11) were acquired, amplified and stocks were prepared for in vitro testing. Both lines were grown in 24 well plates and stimulated with various concentrations of recombinant chicken IFN-γ (CGI). Two separate experiments were performed. In the first experiment, cells were treated with CGI one day after plating. In the second experiment, cells were treated with CGI five days after plating.

Cells were assayed for nitric oxide (NO) production at days 1, 2, 3, 5, 6, 9, 13, and 16 (post-CGI treatment) in the first experiment (i.e., where macrophage were treated with CGI one day after plating). Cells treated with CGI five days after plating were assayed for NO production at days 1, 2, 3, 6, 9, and 15 post-CGI treatment. Samples of culture supernatant were removed from the individual wells and centrifuged at 4,000 RPM for at least five minutes to clarify the supernatants. Determination of NO concentrations were performed in duplicate using the Greiss reagent. Controls from cells not stimulated with CGI were also assayed as blanks for each NO assay. NO production is activated by CGI, and NO production is used here to demonstrate CGI activity. Table 10 sets forth the maximal NO concentration observed, the day (post-CGI addition) maximal NO concentrations were observed, and concentrations of recombinant CGI associated with maximal NO production by the cell lines.

A second set of experiments were performed using cells at day 2 post-plating. The cells were stimulated with recombinant, purified CGI (RCGI), BGI/ARC, CGI/ARC (Batch 1), and CGI/ARC (Batch 2) Cell lines were assayed for NO production three days or four days after stimulation with 10 ng or 100 ng of IFN-γ. These results are set forth in Tables 11 and 12 and FIG. 13. Although less active than CGI, it was surprising to see bovine gamma interferon (BGI) stimulating avian macrophage.

EXAMPLE 12

Avian Administration of ARCs Containing Chicken IFN-γ

CGI/ARCs were prepared as described above and HN plant-derived antigen was prepared according to methods known in the art (see, for example, U.S. Pat. No. 5,310,678 and U.S. Provisional Application 60/467,998, filed May 5, 2003, which are hereby incorporated by reference in its entirety) with the following modification. Plant derived antigen NT 1 cells were harvested 6-12 days after passage. Whole wet NT1 cells harvested directly from cell culture were filtered to remove excess media by placing a Spectramesh 30 filter in a Buchner funnel and pouring cells and media through the filter using a slight vacuum.

To make a preparation of HN vaccine material for assay detection, 0.5 grams of cells were placed in 2 mL of extraction buffer (Dulbecco's phosphate buffered saline (DPBS), 1 mM EDTA, pH 7.2)), and then sonicated for about 2 minutes on ice. Sonication was performed using a Branson 450 sonifier with a replaceable microtip at output control of 8, duty cycle 60 for 2 minutes (for larger preparations, (>5 grams) sonication was performed for 5-10 minutes on ice). Sonicates were then placed on ice until use. Inactivated NDV La Sota strain was derived from allantoic fluid (Lohman Animal Health) at a pre-inactivation egg titer $\geq 10^{10.6}$ EID$_{50}$/mL. The allantoic fluid was stored as a frozen preparation (−80° C.) until use.

For vaccination, SPF chicks from SPAFAS (North Franklin, Conn.) were obtained at one-day of age and placed in cages and allowed to acclimate until 7 days of age. The number of chicks per treatment was based on a completely randomized design using repeat measurements. Any excess chicks were placed randomly in individual cages and were utilized to replace chicks that died from shipping or placement stress. Subcutaneous inoculation was performed by injecting 0.1-0.25 mL into nape of the neck.

Dose and administration of antigen and CGI/ARCs was performed as follows. Plant-derived samples were prepared by hydrating freeze dried CHN extracts in DPBS with 25 μg of CGI/ARC material. Inactivated allantoic fluid was thawed and mixed by adding 25 μg of CGI/ARC directly to the sample. For plant-derived samples containing oil/water emulsion samples, the freeze dried material was resuspended directly into in DPBS containing 0.5% Tween and 2.5% Drakeol Oil with 0.165% Span 80. Two inoculations of antigen were administered, (day 0 at 7-days of age) and a second booster dose at day 14 (21-days of age), the birds were then given an inactivated NDV-infected allantoic fluid (described above) at day 35 (42 days of age) and the trial was terminated at day 42 (49 days of age). A 1 to 2 mL blood sample was collected from each bird via venipuncture of either the jugular or peripheral wing vein on days 14, 21, 35 and 42 of the study.

To measure the immune response, chicken red blood cells in Alsever's solution (CRBC) were obtained from Colorado Serum (L#8152). To prepare a 1% solution of CRBCs, five mL was transferred to a 15 mL conical tube and centrifuged at 250×g for 10 minutes. The supernatant and buffy coat were pipetted from the RBC pellet; the pellet was washed twice by resuspending in 1×DPBS (Dulbecco's Phosphate Buffered Saline) (L# 003435E JRH) and centrifuged 250×g for 10 minutes. The pellet was resuspended to 1% (v/v) in DPBS. To confirm the concentration of the suspension, 400%1 was transferred to 1.6 mL of deionized water and cells lysed by mixing vigorously. The $OD_{540}$ was between 0.4-0.5. The 1% solutions were stored at 2-7° C. until used.

To test hemagglutination, a 96-well U-bottom dish (Falcon) was first sprayed with Static Guard® and blotted onto paper towels. Virus samples were prediluted in DPBS 1:2 and 50 µl of DPBS were placed to each well of the 96-well dish. The diluted virus was added to the first row and then serially diluted 2-fold for the desired number of dilutions per virus sample. 50 µl of 1% CRBC was added to each well and the plate was mixed for 20 seconds at 600 rpm. The plate was placed on wet paper towels and incubated until the CRBCs in the control wells (DPBS and CRBCs at 1:1 ratio) pellet to the bottom of the plate, or for at least 1 hr at 2-7° C. The end point was the dilution of the last well in the series that provides 100% agglutination.

Virus was prediluted in DPBS to provide 4-8 HA units per 50 µl (based on titering the virus described above). A separate plate was set up using 25 µl of DPBS per well in columns 1 and 3-12; 25 µl of serum was added per well in column 1 and 3; serum in column 3 was serially diluted 2 fold through 10 wells. The pretitered virus (25 µl) was then added in all wells column 3-12 and mixed 20 seconds at 600 rpm; the plate was allowed to incubate at room temperature for 1 h+/−15 minutes. Fifty µl of 1% CRBC was then added per well, mixed 20 seconds at 600 rpm and incubated in a humidifying chamber overnight at 2-7° C. for AIV or 1-2 hours at 2-7° C. for NDV. The titer of the serum is the last well in the series dilution that inhibits agglutination 100%.

The serum geometric mean titer (GMT) was determined for each treatment group using Microsoft Excel 2000 version 9.0.3821 SR-1. Background ELISA titers of <10 were given a value of 1 for these calculations. Difference in least squares means of treated birds and controls were determined using least squares analysis. A treatment was passed as effective if there was a significant difference of a treatment group with the non-vaccinated challenge control group.

The HI titer at each bleed date is shown in Table 13. At day 21 (7 days after second dose) there was a 4-fold higher HI titer using a 20 µg dose of the plant derived HN protein when administered with IFN-γ, and a 2-fold increase when combined with an oil/water emulsion. The results indicated an antigen co-administered with IFN-γ(CGI/ARC) can induce an enhanced serum response to a target antigen when compared to the antigen administered without CGI/ARC (see Table 13).

REFERENCE LIST

1. Ada, G. and G. Karupiah. 1997. Overview of Host Defense Mechanisms with Special Reference to Viral Infections, p. 1-18. In G. Karupiah (ed.), Gamma Interferon in Antiviral Defense. Chapman & Hall, New York.
2. Anderson, K. P., E. H. Fennie, and T. Yilma. 1988. Enhancement of a secondary antibody response to vesicular stomatitis virus "G+ protein by IFN-gamma treatment at primary immunization. J.Immunol. 140:3599-3604.
3. Babiuk, L. A., L. M. Sordillo, M. Campos, H. P. A. Hughes, A. Rossi-Campos, and R. Harland. 1991. Application of interferons in the control of infectious diseases of cattle. Journal of Dairy Science 74:4385-4398.
4. Barnes, Andrew C. and Cummings, Susan G. Cellular encapsulation of biological pesticides. 86300128[US 693080 1985-01-22]. 7-15-1992. 1-9-1986. Ref Type: Patent
5. Cerretti, D. P., K. McKereghan, A. Larsen, D. Cosman, S. Gillis, and P. E. Baker. 1986. Cloning, Sequence, and Expression of Bovine Interferon-Gamma. J.Immunol. 136:4561-4564.
6. Fox, L. K., H. D. Liggit, T. Yilma, and L. B. Corbeil. 1990. The effect of interferon-gamma intramammary administration on mammary phagocyte function. Zentralbl.Veterinarmed. 37:28-30.
7. Fransen, L., M. R. Ruysschaert, J. van der Heyden, and W. Fiers. 1986. Recombinant tumor necrosis factor: Species specificity for a variety of human and murine transformed cell lines. Cell Immunol. 100:260-267.
8. Friedman, R. M. and S. N. Vogel. 1983. Interferons with special emphasis on the immune system. Adv. Immunol. 34:97-140.
9. Gaertner, F. H., T. C. Quick, and M. A. Thompson. 1993. CellCap: An Encapsulation System for Insecticidal Biotoxin Proteins, p. 73-83. In L. Kim (ed.), Advanced Engineered Pesticides. Marcel Dekker, Inc., New York.
10. Gough, R. E., W. H. Allan, D. J. Knight, and J. W. G. Leiper. 1975. Further studies on the adjuvant effect of an interferon inducer brl-5907 on newcastle disease and avian influenza inactivated vaccines. J. Immunol. 19:185-188.
11. Gresser, I., C. Maury, and F. Belardelli. 1987. Anti-tumor effects of interferon in mice injected with interferon-sensitive and interferon-resistant friend leukemia cells vi. Adjuvant therapy after surgery in the inhibition of liver and spleen metastases. Proc. Natl. Acad. Sci. U.S.A 39:789-792.
12. Knight, E. J. 1976. Antiviral and cell growth inhibitory activities reside in the same glycoprotein of human fibroblast interferon. Nature 262:302-303.
13. Lofthouse, S. A., A. E. Andrews, M. H. Elhay, V. M. Bowles, E. N. T. Meeusen, and A. D. Nash. 1996. Cytokines as adjuvants for ruminant vaccines. International Journal for Parasitology 26:835-842.
14. Michalski, W. P., B. J. Shiell, T. E. O'Neil, G. Beddome, and J. W. Lowenthal. 1999. Recombinant chicken IFN-gamma expressed in *Escherichia coli*: analysis of C-terminal truncation and effect on biologic activity. J. Interferon Cytokine Res. 19:383-392.
15. Opdenakker, G., Y. Cabeza-Arvelaiz, and J. Van Damme. 1989. Interaction of interferon with other cytokines. Experientia 45:513-520.
16. Perussia, B., E. T. Dayton, R. Lazarus, V. Fanning, and G. Trinchieri. 1983. Immune interferon induces the receptor for monomeric IgG1 on human monocytic and myeloid cells. Cell Immunol. 154:287-295.

17. Pestka, S., J. A. Langer, K. C. Zoon, and C. E. Samuel. 1987. Interferons and their actions. Annu. Rev. Biochem. 56:727-777.
18. Pighetti, G. M. and L. M. Sordillo. 1996. Specific immune responses of dairy cattle after primary inoculation with recombinant bovine interferon-gamma as an adjuvant when vaccinating against mastitis. American Journal of Veterinary Research 57 :819-824.
19. Rammler, David H., Gaertner, Frank H., and Edwards, David L. Pseudomas hosts transformed with bacillus endotoxin genes. Mycogen Corporation. 980129[05281532]. 1-25-1994. 11-23-1992. Ref Type: Patent R. M. Chanock, H. Glensburg, and R. Lerner (eds.), Vaccines 87. Modern approaches to new vaccines including prevention of AIDS. Cold Spring Harbor, N.Y.

24. Yilma, T., S. Owens, E. H. Fennie, and K. P. Anderson. 1989. Enhancement of primary and Secondary Immune Responses by Interferon-gamma. Adv. Exp. Med. Biol. 251:145-152.

25. Yip, Y. K., H. C. Kelker, K. T. Pearlstein, and J. Vilcek. 1984. Purification and structural-functional characterization of human immune interferon. 3:283.

Zuffa, A. and N. Feketeova. 1980. Protection of cattle vaccinated with inactivated oil adjuvant infectious bovine tracheitis vaccine against experimental infection. 27:725-733.

TABLE 1

Factors Involved in Immune Response

| FAMILY | MEMBERS | OTHER NAMES |
|---|---|---|
| Interferons (IFN) | IFN - α | Leukocyte Interferon |
| | IFN - β | Fibroblast Interferon |
| | IFN - γ | Immune Interferon |
| Tumor Necrosis Factors (TNF) | TNF | TNF - α, Cachectin |
| | Lymphotoxin | TNF - β |
| Interleukins (IL) | IL-1 α, IL-1 β | Endogenous Pyrogen, Lamphocyte - Activating Factor, Leukocyte Endogenous Mediator, Hemopoietin 1 |
| | IL-2 | T-Cell Growth Factor |
| | IL-3 | Multipotential CSF, Mast Cell Growth Factor |
| | IL-4 | B-Cell Stimulatory Factor 1 (BSF-1) |
| | IL-5 | T-Cell Replacing Factor (TRF) Eosinophil Differentiation Factor, B-Cell Growth Factor-II (BCGF-II) |
| | IL-6 | B-Cell Stimulatory Factor 2 (BSF-2), Interferon-$\beta_2$ Hepatocyte-Stimulating Factor (HSF) |
| Colony-Stimulating Factors (CSF) | Granulocyte Macrophage-CSF (GM-CSF) | CSF-2 |
| | Granulocyte-CSF (G-CSF) | Pluripoietin |
| | Macrophage-CSF (M-CSF) | CSF-1 |
| | Erythropoietin | |
| Other Growth and Regulatory Factors (GF) | Epidermal Growth Factor (EGF) | |
| | Fibroblast Growth Factor (Acidic-and-Basic-FGF) | |
| | Insulin-like Growth Factor-1 (IGF-1) | Somatomedin C |
| | Insulin-like Growth Factor-2 (IGF-2) | Somatomedin A |
| | Nerve Growth Factor (NFG) | |
| | Platelet-Derived Growth Factor (PDGF) | |
| | Transforming Growth Factor-α (TGF-α) | |
| | Transforming Growth Factor-β (TGF-β) | |

20. Sordillo, L. M. and L. A. Babiuk. 1990. Controlling acute experimental *Escherichia coli* mastitis with recombinant bovine interferon-gamma. Journal of Dairy Science 73:212.

21. Steinbeck, M. J., J. A. Roth, and M. L. Kaeberle. 1986. Activation of bovine neutrophils by recombinant interferon-gamma. Cell Immunol. 98:137-144.

22. Vilcek, J. and E. Demaeyer. 1985. Interferon Vol. 2: Interferon and the Immune System. Elsevier, Amsterdam.

23. Yilma, T., K. Anderson, K. Brechling, and B. Moss. 1987. Expression of an adjuvant gene interferon-gamma in infectious vaccinia virus recombinants, p. 393-396. In

TABLE 2

Virus Challenge Assay

| Sample | Interferon | Antiviral Titre |
|---|---|---|
| ARC control (untransformed, amended cells of MB324) | None | $<10^3$ |
| BAI/ARC (BAI-transformed, amended cells of MB324) | 0.36 mg/mL. | $10^3$ |
| BGI/ARC (BGI-transformed, amended cells of MB324) | 1.8 mg/mL | $10^{6.5}$ |

TABLE 2-continued

Virus Challenge Assay

| Sample | Interferon | Antiviral Titre |
|---|---|---|
| BGI/ARC + BAI/ARC (1.26 mg γ + 0.54 mg α) | 1.8 mg/mL | $10^{7.5}$ |
| Extract control (untransformed, extract of MB324) | None | $<10^3$ |
| BGI extract (BGI-transformed, extract of MB324) | 0.41 mg/mL | $10^6$ |

TABLE 3

Virus Challenge Assay

| Sample | Interferon | Antiviral Titre |
|---|---|---|
| ARC control #1 (untransformed MB324, amended cells) | None | $<10^2$ |
| ARC control #2 (pMYC1803-transformed MB324, amended cells) | None | $<10^2$ |
| BGI/ARC (BGI-transformed MB324, amended cells) | 1.8 mg/mL | $10^7$ |
| P. fluorescens purified BGI | 1.6 mg/mL | $10^{7.3}$ |
| E. coli purified BGI | 2.0 mg/mL | $10^{7.5}$ |

TABLE 4

MHC Class II induction Assay with Bovine Kidney Cells

| Total ARC protein (pg) | MB324/ARC Vector Control Cells BGI (pg)/MHC % | BGI/ARC BGI-Transformed Cells BGI (pg)/MHC % |
|---|---|---|
| 66000000 | 0/21 | 22000.00/100 |
| 6600000 | 0/21 | 2200.00/100 |
| 660000 | 0/21 | 220.00/100 |
| 66000 | 0/20 | 22.00/99 |
| 6600 | 0/20 | 2.20/90 |
| 660 | 0/19 | 0.22/60 |

| BGI protein (pg) | BGI/ARC BGI-Transformed Cells MHC % | Pure BGI from P. fluorescens (DAS std.) MHC % | Pure BGI from E. coli (control) MHC % |
|---|---|---|---|
| 0 | 20 | 20 | 20 |
| 22 | — | 30 | — |
| 220 | 60 | 60 | 40 |
| 2200 (2.2 ng) | 85 | 80 | 60 |
| 22000 | 93 | 90 | 80 |
| 220000 | 98 | 98 | 98 |
| 2200000 (2.2 ìg) | 99 | 99 | — |
| 22000000 | 100 | | |

TABLE 5

Group Designations and Treatments

Group A

Contents: 6 mL/vial    BGI/ARC    Calculated BGI dose
Dose: Inject 1 mL SC on right (0.5 mL/animal)    4800 μg/animal
side of neck.

Group B

Contents: 6 mL/vial    BGI/ARC    Calculated BGI dose
Dose: Inject 1 mL SC on right (0.05 mL/animal)    480 μg/animal
side of neck..

TABLE 5-continued

Group Designations and Treatments

Group C

Contents: 6 mL/vial    BGI/ARC    Calculated BGI dose
Dose: Inject 1 mL SC on right (0.005 mL/animal)    48 μg/animal
side of neck.

Group D

Contents: 6 mL/vial    ARC Control    Calculated BGI dose
Dose: Inject 1 mL SC on right (0.5 mL/animal)    0 μg/animal
side of neck.

TABLE 6

Serum Haptoglobin (ng/mL)

| Group/Dose | | Day 0 | Day 2 | Day 4 |
|---|---|---|---|---|
| | Cow # | | | |
| A | 345 | 3414.732 | 343278 | 339763 |
| IFN-γ/ARC | 349 | 14621.58 | 314864 | 313533 |
| 4800 μg | 362 | 8043.093 | 329346 | 341830 |
| | 377 | 33402.99 | 330788 | 332746 |
| B | 331 | 2442.108 | 299233.1 | 314455 |
| IFN-γ/ARC | 332 | 431.2447 | 304025 | 318863 |
| 480 μg | 347 | 4095.792 | 279063 | 302801 |
| | 351 | 3386.858 | 289166 | 148700 |
| | 376 | 12092.41 | 318965 | 318863 |
| C | 333 | 1145.308 | 293940 | 222203 |
| IFN-γ/ARC | 356 | 30964.4 | 301475 | 279036 |
| 48 μg | 365 | 11002.64 | 328728 | 336975 |
| | 375 | 30780.89 | 284906 | 194211 |
| | 378 | 9255.905 | 266531 | 182632 |
| D | 328 | 4226.292 | 17537.6 | 27173.22 |
| IFN-γ/ARC | 329 | 949.357 | 22061.81 | 29538 |
| 0 μg | 344 | 1125.977 | 10012.77 | 59289.64 |
| | 355 | 11862.54 | 18949.82 | 15312.98 |
| | 371 | 10119.1 | 107177 | 62724 |
| Group | | | | |
| Mean | A | 14870.6 | 329569.0 | 331968.0 |
| | B | 4489.7 | 298090.4 | 280736.4 |
| | C | 16629.8 | 295116.0 | 243011.4 |
| | D | 5656.7 | 35147.8 | 38807.6 |
| SD | A | 13182.9 | 11629.1 | 12890.2 |
| | B | 4467.6 | 15115.9 | 74102.4 |
| | C | 13523.5 | 22874.3 | 64395.4 |
| | D | 5078.4 | 40508.4 | 21004.7 |
| Median | A | 11332.3 | 330067.0 | 336254.5 |
| | B | 3386.9 | 299233.1 | 314455.0 |
| | C | 11002.6 | 293940.0 | 222203.0 |
| | D | 4226.3 | 18949.8 | 29538.0 |

TABLE 7

Serum 2'5'A Synthetase levels (pMol/dL)

| Group | | Day 0 | Day 2 | Day 4 |
|---|---|---|---|---|
| | Cow # | | | |
| A | 345 | 169.4 | 54.8 | 103.7 |
| IFN-γ/ARC | 349 | 81.1 | 26.6 | 300.1 |
| 4800 μg | 362 | 1227.1 | 73.0 | 138.0 |
| | 377 | 439.4 | 407.5 | 646.7 |
| B | 331 | 137.7 | 59.8 | 185.7 |
| IFN-γ/ARC | 332 | 135.1 | 218.4 | 70.7 |
| 480 μg | 347 | 164.5 | 89.3 | 86.0 |
| | 351 | 311.7 | 219.3 | 244.4 |
| | 376 | 391.0 | 618.4 | 195.1 |
| C | 333 | 142.5 | 71.5 | 143.4 |
| IFN-γ/ARC | 356 | 537.5 | 50.1 | 66.6 |

TABLE 7-continued

Serum 2'5'A Synthetase levels (pMol/dL)

| Group | | Day 0 | Day 2 | Day 4 |
|---|---|---|---|---|
| 48 μg | 365 | 105.7 | 355.3 | 144.8 |
| | 375 | 81.8 | 48.4 | 59.7 |
| | 378 | 249.9 | 142.8 | 87.4 |
| D | 328 | 358.2 | 143.8 | 119.3 |
| IFN-γ/ARC | 329 | 393.1 | 16.2 | 41.5 |
| 0 μg | 344 | 132.8 | 203.6 | 47.3 |
| | 355 | 94.3 | 129.6 | 263.1 |
| | 371 | 76.0 | 234.5 | 206.4 |
| | Group | | | |
| Mean | A | 479.2 | 140.5 | 297.1 |
| | B | 228.0 | 241.1 | 156.4 |
| | C | 223.5 | 133.6 | 100.4 |
| | D | 210.9 | 145.5 | 135.5 |

TABLE 7-continued

Serum 2'5'A Synthetase levels (pMol/dL)

| Group | | Day 0 | Day 2 | Day 4 |
|---|---|---|---|---|
| SD | A | 521.4 | 179.1 | 248.3 |
| | B | 116.6 | 223.2 | 74.8 |
| | C | 187.0 | 129.7 | 41.2 |
| | D | 152.3 | 84.1 | 97.7 |
| Median | A | 304.4 | 63.9 | 219.0 |
| | B | 164.5 | 218.4 | 185.7 |
| | C | 142.5 | 71.5 | 87.4 |
| | D | 132.8 | 143.8 | 119.3 |

TABLE 8

CHEMOKINES

| Reference | Protein | Function |
|---|---|---|
| BCA-1/BLC-1 | B Cell-Attracting chemokine-1 (B-Lymphocytes Chemoattracting) (CXCL13) | B-cell attractant |
| BRAK/Kec | CXC chemokine in breast and kidney/Kidney-expressed chemokine (SCYB14, CXCL14) | Involved in MΦ development |
| CXCL16 | CXC-chemokine 16 | |
| ENA-78/LIX | Epithelial cell-derived neutrophil-activating protein 78 (CXCL5, SCYB5) | Neutrophil activating peptide |
| Eotaxin-1 | Eotaxin-1 (CCL11) | Eosinophil chemotaxis |
| Eotaxin-2/MPIF-2 | Eotaxin-2 (CCL24, CKβ6) | Chemotactic agent for T-cells and eosinophils |
| Exodus-2/SLC | Exodus-2 (CCL21, CKβ9, SCYA21) | Angiostatic activity, chemotacitc agent for T-cells, dendritic cells, CD34+ hematopoietic cells, NK cells, and B-cells |
| Fractalkine/Neurotactin | Fractalkine/Neurotactin (CX3CL1) | Chemotactic agent for T-cells and monocytes |
| GROalpha/MGSA | Melanoma Growth Stimulatory Activity protein (CXCL1) | Neutrophil activation |
| HCC-1 | Hemofiltrate CC chemokine 1 (SCYA14, CCL14) | Chemotactic agent for monocytes and THP-1 cells |
| IL8 | Interleukin 8 (CXCL8) | Chemoattractant for neutrophils, basophils, and T-cells; activates neutrophils |
| I-TAC | Interferon-stimulated T-cell alpha chemoattractant (CXCL11) | |
| Lymphotactin/ATAC/SCM | Lymphotactin (CL1, LTN) | Chemoattractant for T and NK cells |
| MCP-1/MCAF | Monocyte Chemotactic Protein 1 (CCL2, SCYA2) | Chemoattractant for monocytes and neutrophils; augments neutrophil anti-tumor activity |
| MCP-3 | Monocyte Chemotactic Protein 3 (CCL7, SCYA7) | Chemoattractant for monocytes and eosinophils; augments monocyte anti-tumor activity |
| MCP-4 | Monocyte Chemotactic Protein 4 (CCL13, SCYA13) | Chemoattractant for monocytes, lymphocytes, basophils, and eosinophils |
| MDC/STCP-1/ABCD-1 | Macrophage-Derived Chemokine (CCL22, SCYA22) | Chemoattractant for T-cells, activated lymphocytes, and monocytes |
| MIP-1α | Macrophage Inflammatory Protein 1 alpha (CCL3, SCYA3) | Chemoattractant for lymphocytes |
| MIP-1β | Macrophage Inflammatory Protein 1 beta (CCL4, SCYA4) | Chemoattractant for moncytes, densritic cells, NK cells and T-cells |
| MIP-2α/GROβ | Macrophage Inflammatory Protein 2 alpha (CXCL2) | |

TABLE 8-continued

CHEMOKINES

| Reference | Protein | Function |
|---|---|---|
| MIP-3α/Exodus/LARC | Macrophage Inflammatory Protein 3 alpha (CCL20, SCYA20) | Chemoattractant for lymphocytes, activated NK cells, dendritic cells |
| MIP-3β/Exodus-3/ELC | Macrophage Inflammatory Protein 3 beta (CCL19, SCYA19) | Chemoattractant for T-cells, B-cells, and dendritic cells |
| MIP-4/PARC/DC-CK1 | Macrophage Inflammatory Protein 4 (CCL18, CKβ7, SCYB18) | Chemoattractant for T-cells |
| RANTES | Rantes, formerly "T cell-specific protein" (CCL5) | Chemoattractant for memory T-cells, monocytes, and eosinophils |
| SDF1α | Stroma Cell-Derived Factor 1 Alpha | Chemoattractant for neutrophils, lymphocytes, and monocytes |
| TARC | Thymus and Activation-Regulated Chemokine (CCL17) | Chemoattractant for activated $T_{H2}$-cells |
| TECK | Thymus-Expressed Chemokine (CCL25) | Chemoattractant for thymocytes, MΦ, Thp-1 cells, and dendritic cells |

TABLE 9

CYTOKINES

| Reference | Protein | Function |
|---|---|---|
| GM-CSF | Macrophage Colony Stimulating Factor | Growth and differentiation of hematopoietic lineages (e.g., granulocytes, MΦ, eosinophils, and erythrocytes |
| IFN alpha | Interferon Alpha | Anti-tumor and anti-viral activity |
| IFN beta | Interferon Beta | Antiviral, antibacterial, and anticancer activity |
| IFN gamma | Interferon Gamma | Stimulates CTL responses; antiviral and anti-proliferative activity on transformed cells |
| Interleukins | | |
| IL-1 beta | Interleukin-1 Beta | Stimulates B-cell maturation/proliferation |
| IL-2 | Interleukin-2 | Regulates immune response and T-cell proliferation |
| IL-4 | Interleukin-4 | Activates B-cells |
| IL-6 | Interleukin-6 | B-cell differentiation |
| IL-10 | Interleukin-10 | Immunosupressive and anti-inflammatory |
| IL-12elasti | Interleukin-12 (with elastin linker between subunits) | Growth factor for activated T-cells and MNK cells; enhances lytic activity of NK/LAK cells |
| IL-13 | Interleukin-13 | Anti-inflammatory agent |
| IL-15 | Interleukin-15 | Stimulates T-lymphocyte and NK proliferation |
| IL-16 | Interleukin-16 | Chemoattractant for CD4 lymphocytes, monocytes, dendritic cells, and eosinophils |
| IL-18 | Interleukin-18 | Induces IFN-γ and augments NK activity |
| IL-18BPa | Interleukin-18 binding protein, isoform A | Inhibitor of early Th1 cytokine response |
| IL-23 | Interleukin-23 | Stimulates proliferation of memory T-cells; stimulates IFN-γ production |
| IL-24 | Interleukin-24 | |
| VIP | Vasoactive Intestinal Peptide | Vasodialator; lowers arterial blood pressure; stimulates myocardial contractility; smooth muscle relaxant; MΦ activator; stimulates T-cell proliferation |
| TNF Superfamily | | |
| LIGHT/TNFSF14 | Tumor Necrosis Factor SuperFamily member 14 | Induces apoptosis, stimulates T-cells, suppresses in vivo tumor formation |
| sTALL-1/TNFSF13B (also called BLyS, BAFF, THANK) | Tumor Necrosis Factor SuperFamily member 13B | Stimulates B-cell proliferation |
| TNFalpha/TNFSF2 | Tumor Necrosis Factor Alpha | Cytolysis of tumor cells; induces cell differentiation |
| TWEAK/TNFSF12 | Tumor Necrosis Factor SuperFamily member 12 (also called Apo3L) | Induces tumor cell death, influences astrocyte behavior |

TABLE 10

NO production in avian macrophage stimulated with purified recombinant CGI

| Cell Line | CGI concentration (μg) | NO concentration (μM) | Days after CGI addition |
|---|---|---|---|
| HD11 (one day) | 12.5 | 40.68 | 13 |
| HD11 (5 days) | 12.5 | 145.38 | 2 |
| MQ-NCSU (one day) | 1.0 | 30.41 | 5 |
| MQ-NCSU (5 days) | 12.5 | 35.08 | 2 |

TABLE 11

NO production (μM), after three days, in avian macrophage treated with 100 ng IFN-γ

| Cell Line | RCGI | BGI/ARC | CGI/ARC (Batch 1) | CGI/ARC (Batch 2) |
|---|---|---|---|---|
| HD11 | [NO] = 3.4 | [NO] = 17.2 | [NO] = 59.5 | [NO] = 81.1 |
| MQ-NCSU | [NO] = 17.8 | [NO] = 53.90 | [NO] = 76.5 | [NO] = 84.9 |

TABLE 12

NO production (μM), after four days, in avian macrophage treated with 10 ng IFN-γ

| Cell Line | RCGI | BGI-ARC | CGI/ARC (Batch 1) | CGI/ARC (Batch 2) |
|---|---|---|---|---|
| HD11 | [NO] = 0.5 | [NO] = 2.4 | [NO] = 2.4 | [NO] = 16.8 |
| MQ-NCSU | [NO] = 6.7 | [NO] = 28.0 | [NO] = 53.8 | [NO] = 72.6 |

TABLE 13

Avian Immune Response to Plant Cell Derived HN in presence of chicken IFN-γ(CGI/ARC)

| Treatment Group Description | NDV HI GMT Day 14 | Day 21 | Day 35 | Day 42 |
|---|---|---|---|---|
| pHN (20 μg) SQ | 1 | 19 | 43 | 8 |
| pHN (20 μg) + CGI/ARC (25 μg) SQ | 1 | 76 | 91 | 13 |
| pHN (20 μg) + CGI/ARC (25 μg) SQ Oil in Water Emulsion | 2 | 38 | 71 | 17 |
| Inactivated NDV derived from allantoic fluid + CGI/ARC (25 μg) SQ | 1 | 6 | 5 | 25 |
| NT Control + CGI/ARC (25 μg) IN/Ocular & SQ Oil in Water Emulsion | 1 | 1 | 1 | 2 |

```

We claim:

1. An amended recombinant cell (ARC) comprising at least one heterologous gene, said at least one heterologous gene encoding a chemokine or a cytokine, wherein said amended recombinant cell is *Pseudomonas fluorescens*.

2. The ARC according to claim 1, wherein said ARC further comprises at least one additional heterologous gene encodes IL-1, IL-2, IL-3, IL-4, IL-5, IL-6, IL-7, IL-8, IL-9, IL-10, IL-11, IL-15, Il-16, Il-18, IL-23, IL-24, erythropoietin, G-CSF, M-CSF, platelet derived growth factor (PDGF), MSF, FLT-3 ligand, EGF, fibroblast growth factor (FGF); aFGF (FGF-1); bFGF (FGF-2); FGF-3; FGF-4; FGF-5; FGF-6; FGF-7; insulin-like growth factor 1 (IGF-1); IGF-2; vascular endothelial growth factor (VEGF); IFN-γ; IFN-α; IFN-β; leukemia inhibitory factor (LIF); ciliary neurotrophic factor (CNTF); oncostatin M; stem cell factor (SCF); TGF-α; TGF-β1; TGFβ2; a chemokine selected from the group consisting of BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF1α, TARC, and TECK; or those cytokines or chemokines provided in Tables 1, 8, and 9.

3. The ARC according to claim 1, wherein said at least one heterologous gene encodes IFN-γ.

4. The ARC according to claim 3, wherein said IFN-γ is bovine, avian, fish, or human.

5. The ARC according to claim 4, wherein said IFN-γ is bovine.

6. The ARC according to claim 4, wherein said avian IFN-γ is chicken IFN-γ.

7. The ARC according to claim 2, wherein said at least one additional heterologous gene encodes IFN-α.

8. A composition comprising an ARC according to claim 1 and a carrier.

9. A method of inducing or accelerating an immune response in an individual to an antigen or immunogen comprising the step of administering, to an individual:
    amended recombinant *Pseudomonas fluorescens* cells (ARCs) comprising at least one heterologous gene encoding a chemokine or a cytokine; or
    a composition comprising amended recombinant *Pseudomonas fluorescens* cells (ARCs) comprising at least one heterologous gene encoding a chemokine or a cytokine.

10. The method according to claim 9, wherein said method further comprises the administration of an antigen of interest.

11. The method according to claim 10, further comprising the administration of lipopolysaceharide (LPS).

12. The method according to claim 9, wherein said heterologous gene encodes IFN-γ.

13. The method according to claim 12, wherein said IFN-γ is bovine, avian, fish, or human.

14. The method according to claim 13, wherein said IFN-γ is bovine.

15. The method according to claim 13, wherein said avian IFN-γ is chicken IFN-γ.

16. The method according to claim 9, wherein the ARCs co-express at least one antigen of interest.

17. The ARC according to claim 3, wherein said ARC further comprises at least one additional heterologous gene that encodes IFN-α.

18. The method according to claim 9, wherein said ARCs further comprise at least one additional heterologous gene that encodes IL-1, IL-2, IL-3, IL-4, IL-5, IL-6, IL-7, IL-8, IL-9, IL-10, IL-11, IL-15, Il-16, Il-18, IL-23, IL-24, erythropoietin, G-CSF, M-CSF, platelet derived growth factor (PDGF), MSF, FLT-3 ligand, EGF, fibroblast growth factor (FGF); aFGF (FGF-1); bFGF (FGF-2); FGF-3; FGF-4; FGF-5; FGF-6; FGF-7; insulin-like growth factor 1 (IGF-1); IGF-2; vascular endothelial growth factor (VEGF); IFN-γ; IFN-α; IFN-β; leukemia inhibitory factor (LIF); ciliary neurotrophic factor (CNTF); oncostatin M; stem cell factor (SCF); TGF-α; TGF-β1; TGF-β2; a chemokine selected from the group consisting of BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF1α, TARC, and TECK; or a cytokine or chemokine as provided in Tables 1, 8, and 9.

19. The method according to claim 18, wherein said at least one additional heterologous gene encodes IFN-α.

20. The method according to claim 12, wherein said ARCs further comprise at least one additional heterologous gene that encodes IFN-α.

* * * * *

UNITED STATES PATENT AND TRADEMARK OFFICE
CERTIFICATE OF CORRECTION

PATENT NO.       : 7,338,794 B2
APPLICATION NO.  : 10/681540
DATED            : March 4, 2008
INVENTOR(S)      : Frank H. Gaertner et al.

It is certified that error appears in the above-identified patent and that said Letters Patent is hereby corrected as shown below:

Column 4,
Line 8, "2α/GROP" should read --2α/GROβ--.

Column 11,
Lines 17-18, "1'-16, 11-18" should read --11-16, 11-18--.

Column 23,
Line 17, "MVP(T" should read --MVP®--.

Column 24,
Line 48, "$\geq 10^{10.6}$" should read --$\geq 10^{10.6}$--.

Column 25,
Line 20, "400%1" should read --400μ1--.

Column 28,
Lines 13-14, "bovine tracheitis" should read --bovine rhino tracheitis--.

Column 32,
Table 8, MCP-1/MCAF reference, Function column, "aguments neutrophil" should read --augments neutrophil--.
Table 8, MIP-1β Reference, Function column, "moncytes, densritic" should read --monocytes, dendritic--.

Column 37,
Lines 58-59, "gene encodes" should read --gene that encodes--.

Column 38,
Lines 60-61, "those cytokines or chemokines" should read --a cytokine or chemokine as--.

UNITED STATES PATENT AND TRADEMARK OFFICE
CERTIFICATE OF CORRECTION

PATENT NO. : 7,338,794 B2
APPLICATION NO. : 10/681540
DATED : March 4, 2008
INVENTOR(S) : Frank H. Gaertner et al.

It is certified that error appears in the above-identified patent and that said Letters Patent is hereby corrected as shown below:

Column 39,
Line 21, "lipopolysaceharide" should read --lipopolysaccharide--.

Signed and Sealed this

Fifteenth Day of July, 2008

JON W. DUDAS
*Director of the United States Patent and Trademark Office*

                      SEQUENCE LISTING

<160> NUMBER OF SEQ ID NOS: 3

<210> SEQ ID NO 1
<211> LENGTH: 475
<212> TYPE: DNA
<213> ORGANISM: Artificial Sequence
<220> FEATURE:
<223> OTHER INFORMATION: Synthetic bovine gamma-interferon

<400> SEQUENCE: 1
agagaactag taaaaaggag aaatccatgc agggccaatt ttttagagaa atagaaaact      60
taaaggagta ttttaatgca agtagcccag atgtagctaa gggtgggcct ctcttctcag     120
aaattttgaa gaattggaaa gatgaaagtg acaaaaaaat tattcagagc caaattgtct     180
ccttctactt caaactcttt gaaaacctca agataacca ggtcattcaa aggagcatgg      240
atatcatcaa gcaagacatg tttcagaagt tcttgaatgg cagctctgag aaactggagg     300
acttcaaaaa gctgattcaa attccggtgg atgatctgca gatccagcgc aaagccataa     360
atgaactcat caaagtgatg aatgaccgtg caccaaaatc taacctcaga aagcggaaga     420
gaagtcagaa tctctttcga ggccggagag catcaacgta atgactcgag tctct          475

<210> SEQ ID NO 2
<211> LENGTH: 475
<212> TYPE: DNA
<213> ORGANISM: Artificial Sequence
```

-continued

```
<220> FEATURE:
<223> OTHER INFORMATION: Synthetic bovine gamma-interferon

<400> SEQUENCE: 2
tctcttgatc attttcctc tttaggtacg tcccggttaa aaaatctctt tatcttttga       60
atttcctcat aaaattacgt tcatcgggtc tacatcgatt cccacccgga gagaagagtc    120
tttaaaactt cttaacctt ctactttcac tgttttttta ataagtctcg gtttaacaga    180
ggaagatgaa gtttgagaaa cttttggagt ttctattggt ccagtaagtt tcctcgtacc    240
tatagtagtt cgttctgtac aaagtcttca agaacttacc gtcgagactc tttgacctcc    300
tgaagttttt cgactaagtt taaggccacc tactagacgt ctaggtcgcg tttcggtatt    360
tacttgagta gtttcactac ttactggaca gtggttttag attggagtct ttcgccttct    420
cttcagtctt agagaaagct ccggcctctc gtagttgcat tactgagctc agaga        475

<210> SEQ ID NO 3
<211> LENGTH: 144
<212> TYPE: PRT
<213> ORGANISM: Artificial Sequence
<220> FEATURE:
<223> OTHER INFORMATION: Synthetic bovine gamma-interferon

<400> SEQUENCE: 3

Met Gln Gly Gln Phe Phe Arg Glu Ile Glu Asn Leu Lys Glu Tyr Phe
1               5                   10                  15

Asn Ala Ser Ser Pro Asp Val Ala Lys Gly Gly Pro Leu Phe Ser Glu
            20                  25                  30

Ile Leu Lys Asn Trp Lys Asp Glu Ser Asp Lys Lys Ile Ile Gln Ser
        35                  40                  45

Gln Ile Val Ser Phe Tyr Phe Lys Leu Phe Glu Asn Leu Lys Asp Asn
    50                  55                  60

Gln Val Ile Gln Arg Ser Met Asp Ile Ile Lys Gln Asp Met Phe Gln
65                  70                  75                  80

Lys Phe Leu Asn Gly Ser Ser Glu Lys Leu Glu Asp Phe Lys Lys Leu
                85                  90                  95

Ile Gln Ile Pro Val Asp Asp Leu Gln Ile Gln Arg Lys Ala Ile Asn
            100                 105                 110

Glu Leu Ile Lys Val Met Asn Asp Leu Ser Pro Lys Ser Asn Leu Arg
        115                 120                 125

Lys Arg Lys Arg Ser Gln Asn Leu Phe Arg Gly Arg Arg Ala Ser Thr
    130                 135                 140
```